(12) United States Patent
Baird et al.

(10) Patent No.: US 6,958,240 B1
(45) Date of Patent: Oct. 25, 2005

(54) INHIBITION OF MAJOR GROOVE DNA BINDING PROTEINS BY MODIFIED POLYAMIDES

(75) Inventors: Eldon E. Baird, Foster City, CA (US); Peter B. Dervan, San Marino, CA (US)

(73) Assignee: California Instiute of Technology, Pasadena, CA (US)

( * ) Notice: Subject to any disclaimer, the term of this patent is extended or adjusted under 35 U.S.C. 154(b) by 689 days.

(21) Appl. No.: 09/374,704

(22) Filed: Aug. 12, 1999

Related U.S. Application Data

(63) Continuation-in-part of application No. 08/853,522, filed on May 8, 1997, now Pat. No. 6,635,417, which is a continuation-in-part of application No. 08/837,524, filed on Apr. 21, 1997, now Pat. No. 6,143,901, which is a continuation-in-part of application No. PCT/US97/03332, filed on Feb. 20, 1997, and a continuation-in-part of application No. 08/607,078, filed on Feb. 26, 1996.

(60) Provisional application No. 60/042,022, filed on Apr. 16, 1997, and provisional application No. 60/043,444, filed on Apr. 8, 1997.

(51) Int. Cl.[7] ............................. A61K 7/06; A61K 7/11; C12N 5/00; C07H 5/04
(52) U.S. Cl. ..................... 435/375; 424/70.17; 536/18.7
(58) Field of Search ....................... 424/70.17; 514/44; 536/18.7, 24.3, 24.5; 435/6, 5, 375, 325, 810; 436/501

(56) References Cited

U.S. PATENT DOCUMENTS

| | | | |
|---|---|---|---|
| 5,391,723 A | 2/1995 | Priest | 536/23.1 |
| 5,574,142 A | 11/1996 | Meyer, Jr. et al. | 536/23.1 |
| 5,578,444 A | 11/1996 | Edwards et al. | 435/6 |
| 5,659,022 A | 8/1997 | Kutyavin et al. | 536/22.1 |
| 5,698,674 A | 12/1997 | Bruice et al. | 530/331 |
| 5,801,155 A | 9/1998 | Kutyavin et al. | 514/44 |
| 5,955,590 A | 9/1999 | Levina et al. | 536/23.1 |

FOREIGN PATENT DOCUMENTS

| WO | 92/20698 | 11/1992 |
|---|---|---|
| WO | 98/52614 | 11/1998 |

OTHER PUBLICATIONS

Swalley et al. J. Am. Chem. Soc. 1996, vol. 118, pp. 8198–8206.*
Trauget et al. J. Am. Chem. 1996, vol. 118, pp. 6160–6166.*
Parks et al. J. Am. Chem. Soc. 1996, vol. 118, pp. 6153–6159.*
Akiyama et al., "Microscopic DNA Flexibility Analysis," *J. Biol. Chem.* 271(46):29126–29135 (1996).
Akiyama et al., "Structural Analysis of DNA Bending Induced by Tethered Triple Helix Forming Oligonucleotides," *Biochemistry* 36:2307–2315 (1997).
Akiyama et al., "The design of an agent to bend DNA," *Proc. Natl. Acad. Sci.* 93:12122–12127 (1996).
Alberts et al., eds., *Molecular Biology of The Cell*, 3rd ed. Garland Publishing, NY (1994).
Bailly et al., "Effects of Base Substitutions on the Binding of a DNA–bending Protein," *J. Molecular Biology* 253:1–7 (1995).
Baird and Dervan, "Solid Phase Synthesis of Polyamides Containing Imidazole and Pyrrole Amino Acids," *J. Am. Chem .Soc.* 118:6141–6146 (1996).
Barcelo et al., "Removal of DNA Curving by DNA Ligands: Gel Electrophoresis Study," *Biochemistry* 30:4863–4873 (1991).
Barlos et al., "2–Chlorotrityl chloride resin," *Int. J. Peptide Protein Res.* 37:513–520 (1991).
Bloomfield et al., "Conformational statistics E. Wormlike Chains," *Physical Chemistry of Nucleic Acids* pp. 159–166 (1974).
Bolshoy et al., "Curved DNA without A–A: Experimental estimation of all 16 DNA wedge angles," *Proc. Natl. Acad. Sci.* 88:2312–2316 (1991).
Bond et al., "Conformational Transitions of Duplex and Triplex Nucleic Acid helices: Thermodynamic Analysis of Effects of Salt Concentration on Stability Using Preferential Interaction Coefficients," *Biophysical Journal* 67:825–836 (1994).
Brenowitz et al., "Quantitative Dnase Footprint Titration: A Method for Studying Protein–DNA Interactions" *Methods Enzymol.* 130:132–181 (1986).
Brenowitz et al., "Footprint" titrations yield valid thermodynamic isotherms *Proc. Natl. Acad. Sci. USA* 83:8462–8466 (1986).
Bruice et al., "Rational design of substituted tripyrrole peptides that complex with DNA by both selective minor-groove binding and electrostatic interaction with the phosphate backbone," *Proc. Natl. Acad. Sci. USA* 89:1700–1704 (1992).
Bruice et al., "A Microgonotropen Branched Decaaza Decabutylamine and its DNA and DNA/Transcription Factor Interactions," *Bioorg. Med. Chem.* 5:685–692 (1997).
Chen and Lown, "A New DNA Minor Groove Binding Motif: Cross–Linked Lexitropsins," *J. Am. Chem. Soc.* 116:6995–7005 (1994).
Chen et al., "Binding of two distamycin A molecules in the minor groove of an alternating B–DNA duplex" *M. Struct. Biol. Nat.* 1(3):169–175 (1994).
Chiang et al., "Targeting E2F1–DNA complexes with microgonotropen DNA binding agents," *Proc. Natl. Acad. Sci. USA* 94:2811–2816 (1997).

(Continued)

*Primary Examiner*—John L. LeGuyader
*Assistant Examiner*—Janet L. Epps-Ford
(74) *Attorney, Agent, or Firm*—Foley & Lardner

(57) ABSTRACT

This invention provides improved polyamides comprising a positive patch for contacting the phosphate backbone or major groove of a DNA molecule. As such, the improved polyamides are capable of inhibiting the function or binding of a DNA-binding protein to a DNA molecule. The improved polyamide provides for more efficient function of the polyamide.

25 Claims, 22 Drawing Sheets

OTHER PUBLICATIONS

Cho et al., "Cyclic polyamides for recognition in the minor groove of DNA," *Proc. Natl. Acad. Sci. USA* 92:10389–10392 (1995).

de Clairac et al., "NMR Characterization of Hairpin Polyamide Complexes with the Minor Groove of DNA," *J. Am. Chem. Soc.* 119:7909–7916 (1997).

Deutscher, ed., "Guide to Protein Purification," *Methods in Enzymology* vol. 182, Academic Press, SD CA (1989).

Dlakic et al., "The Organic Crystallizing Agent 2–Methyl–2, 4–pentanediol Reduces DNA Curvature by means of Structural changes in A–tracts," *J. Biological Chem.* 271:17911–17919 (1996).

Duval–Valentin et al., "Specific inhibition of transcription by triple helix–forming oligonucleotides," *Proc. Natl. Acad. Sci.* 89:504–508 (1992).

Dwyer et al., "Structural Analysis of Covalent Peptide Dimers, Bis(pyridine–2–carboxamidonetropsin)($CH_2$)$_{3-6}$, In Complex with 5'–TGACT–3' Sites by Two–Dimensional NMR," *J. Am. Chem. Soc.* 115:9900–9906 (1993).

Ellenberger et al., "The GCN4 Basic Region Leucine Zipper Binds DNA as a Dimer of uninterrupted α helices: Crystal Structure of the protein–DNA Complex," *Cell* 71:1223–1237 (1992).

Feng et al., "Hin Recombinase Bound to DNA: The Origin of Specificity in Major and Minor Groove Interactions," *Science* 263:348–355 (1994).

Fenley et al., "Electrostatic Persistence Length of a Smoothy Bending Polyion Computed by Numerical Counterion Condensation Theory," *J. Physical Chemistry* 96:3963–3969 (1992).

Freshney, *Culture of Animal Cells: A Manual of Basic Technique*, 2$^{nd}$ ed. Alan R. Liss, Inc. NY NY (1987).

Gehring et al., "Homeodomain Proteins," *Annu. Rev. Biochem.* 63:487–526 (1994).

Gehring et al., "Homeodomain–DNA Recognition," *Cell* 78:211–223 (1994).

Geierstanger et al., "Design of a G.C—Specific DNA Minor Groove–Binding Peptide," *Science* 266:646–650 (1994).

Geierstanger et al., "Structural and Dynamic Characterization of the Heterodimeric and Homodimeric Complexes of Distamycin and 1–Methylimidazole–2–carboxamide–Netropsin Bound to the Minor Groove of DNA," *Biochemistry* 33:3055–3062 (1994).

Geierstanger et al., "NMR Characterization of a Heterocomplex Formed by Distamycin and Its Analog 2–ImD with d(CGCAAGTTGGC):d(GCCAACTTGCG): Preference for the 1:1:1 2–ImD:Dst:DNA Complex over the 2:1 2–ImD:DNA and the 2:1 Dst:DNA Complexes," *J. Am. Chem. Soc.* 115:4474–4482 (1993).

Gennaro (editor), *Remington's Pharmaceutical Sciences* (1990) (Table of Contents Only).

Goeddel, ed. "Gene Expression Technology," *Methods in Enzymology* vol. 185, Academic Press, SD CA (1991).

Gottesfeld et al., "Regulation of gene expression by small molecules," *Nature* 387:202–205 (1997).

Graham and Prevec, "Ch. 11—Manipulation of Adenovirus Vectors," in *Methods in Molecular Biology, vol. 7: Gene Transfer and Expression Protocols*, edited by E.J. Murray, The Humana Press, Inc., Clifton, N.J., pp. 109–128 (1991).

Hertzberg and Dervan, "Cleavage of DNA with Methidiumpropyl–EDTA–Iron(II): Reaction Conditions and Product Analyses," *Biochemistry* 23:3934–3945 (1984).

Ho et al., "Specific inhibition of formation of transcription complexes by a calicheamicin oligosaccharide: A paradigm for the development of transcriptional antagonists," *Proc. Natl. Acad. Sci.* 91:9203–9207 (1994).

Hope et al., "Functional Dissection of a Eukaryotic Transcriptional Activator Protein, GCN4 of Yeast," *Cell* 46:885–894 (1986).

Hurst, "Transcription Factors 1: bZIP proteins," *Protein Profile* 2:105–168 (1995).

Iverson and Dervan, "Piperdine specific DNA chemical sequencing reaction," *Nucleic Acids Research* 14:7823–7830 (1987).

Johnston et al., "Autoradiography using storage phosphor technology," *Electrophoresis* 11:355–360 (1990).

Jones et al., "Synthesis and Binding Properties of Pyrimidine Oligodeoxynucleoside Analogs Containing Neutral Phosphodiester Replacements: The Formacetal and 3'–Thioformacetal Internucleoside Linkages," *J. Org. Chem.* 58:2983–2991 (1993).

Kelly et al., "Binding site size limit of the 2:1 pyrrole–imidazole polyamide–DNA motif," *Proc. Natl. Acad. Sci. USA* 93:6981–6985 (1996).

Kielkopf et al., "Structural basis for G–C recognition in the DNA minor groove," *Nature Structural Biology* 5(2):104–109 (1998).

Kim et al., "Crystal structure of a yeast TBP/TATA–box complex," *Nature* 365:512–520 (1993).

Konig et al., "The X–ray Structure of the GCN4–bZIP Bound to ATF/CREB Site DNA Shows the Complex Depends on DNA Flexibility," *J. Mol. Biol.* 233:139–154 (1993).

Larsson et al., "DAPI Staining of DNA: Effect of Change in Charge, Flexibility, and Contour Length on Orientational Dynamics and Mobility of the DNA during Agarose Gel Electrophoresis," *J. Physical Chemistry* 100:3252–3263 (1996).

Lewin, "Interpreting the genetic code," *Genes* VI pp. 213–215 (1997).

Lewin, "Promoters for RNA polymerase II have short sequence elements," *Genes* VI pp. 831–835 (1997).

Liberles et al., "Design of artificial sequence–specific DNA bending ligands," *Proc. Natl. Acad. Sci.* 93:9510–9514 (1996).

Liu et al., "Sequence–selective carbohydrate–DNA interaction: Dimeric and monomeric forms of the calicheamicin oligosaccharide interfere with transcription factor function," *Proc. Natl. Acad. Sci.* 93:940–944 (1996).

Maher et al., "Analysis of Promoter–Specific Repression by Triple–Helical DNA Complexes in a Eukaryotic Cell–Free Transcription System," *Biochemistry* 31:70–81 (1992).

Maher et al., "Kinetic Analysis of Oligodeoxyribonucleotide–Directed Triple–Helix Formation on DNA," *Biochemistry* 29:8820–8826 (1990).

Manning, "Breathing and Bending Fluctuations in DNA Modeled by an Open–Base–Pair Kink Coupled to Axial Compression," *Biopolymers* 22:689–729 (1983).

Maxam et al., Nucleic Acids Part I: "Sequencing End–Labeled DNA with Base–Specific Chemical Cleavages," *Methods Enzymol Vol* 65:499–560 (1980).

McCarthy et al., "Detection of an unusual distortion in A–tract DNA using $KmnO_4$: effect of temperature and distamycin on the altered conformation," *Nucleic Acids Research* 19:3421–3429 (1991).

McKnight et al., eds., "Dangerous Liasions: Fos and Jun, Oncogenic Transcription Factors," & "Yeast GCN4 Transcriptional Activator Protein," *Transcriptional Regulation* pp. 797–859 (1992).

Michael A. Innis et al., *PCR Protocols: A Guide to Methods and Applications,* edited by Michael A. Innis et al., Academic Press, San Diego (1990) (Table of Contents Only).

Moser and Dervan, "Sequence–Specific Cleavage of Double Helical DNA by Triple Helix Formation," *Science* 238:645–659 (1987).

Mrksich and Dervan, "Antiparallel Side–by–Side Heterodimer for Sequence–Specific Recognition in the Mirror Groove of DNA by a Distamycin/1–Methylimidazole–2–carboxamide–netropsin Pair," *J. Am. Chem. Soc.* 115:2572–2576 (1993).

Mrksich and Dervan, "Design of a Covalent Peptide Heterodimer of Sequence–Specific Recognition in the Minor Groove of Double–Helix DNA," *J. Am. Chem. Soc.* 116:3663–3664 (1994).

Mrksich and Dervan, "Enhanced Sequence Specific Recognition in the Minor Groove of DNA by Covalent Peptide Dimers: Bis(pyridine–2–carboxamidonetropsin)(CH$_2$)$_{3-6}$," *J. Am. Chem. Soc.* 115:9892–9899 (1993).

Mrkisch and Dervan, "Recognition in the Minor Groove of DNA at 5'–(A,T)GCGC(A,T)–3' by a Four Ring Tripeptide Dimer. Reversal of the Specificity of the Natural Product Distamycin," *J. Am. Chem. Soc.* 117:3325–3332 (1995).

Mrksich et al. "Antiparallel side–by–side dimeric motif for sequence–specific recognition in the minor groove of DNA by the designed peptide 1–methylimidazole–2–carboxamide netropsin," *Proc. Natl. Acad. Sci. USA* 89:7586–7590 (1992).

Mrksich et al., "Hairpin Peptide Motif: A New Class of Oligopeptides for Sequence–Specific Recognition in the Minor Groove of Double–Helical DNA," *J. Am. Chem. Soc.* 116:7983–7988 (1994).

Nielsen, "Design of Sequence–Specific DNA–Binding Ligands," *Chem. Eur. J.* 3:505–508 (1997).

Oakley et al., "Evidence That a Minor Groove–Binding Peptide and a Major Groove–Binding Protein Can Simultaneously Occupy a Common Site on DNA," *Biochemistry* 31:10969–10975 (1992).

Oakley et al., "Structural Motif of the GCN4 DNA Binding Domain Characterized by Affinity Cleaving," *Science* 248:847–850 (1989).

Paolella et al., "DNA Targets for Certain bZIP Proteins Distinguished by an Intrinsic Bend," *Science* 264:1130–1133 (1994).

Park et al., "Drug binding to higher ordered DNA structures: Netropsin complexation with a nucleic acid triple helix," *Proc. Natl. Acad. Sci.* 89:6653–6657 (1992).

Parks et al., "Simultaneous Binding of a Polyamide Dimer and an oligonucleotide in the Minor and major Grooves of DNA," *Bioorganic & Medicinal Chemistry* 4:1045–1050 (1996).

Parvin et al. "Pre–bending of a promoter sequence enhances affinity for the TATA–binding factor," *Nature* 373:724–727 (1995).

Pelton, "Structural characterization of a 2:1 distamycin A:d(CGCAAATTGGC) complex by two–dimensional NMR," *Proc. Natl. Acad. Sci.* 86:5723–5727 (1989).

Pelton and Wemmer, "Binding Modes of Distamycin A with d(CGCAAATTTGCG)$_2$ Determined by Two–Dimensional NMR," *J. Am. Chem. Soc.* 112:1393–1399 (1990).

Philpott et al., "Screening of Charged Electrodes in Aqueous Electrolytes," *J. Electrochem. Soc.* 142:L25–L28 (1995).

Perez–Martin et al., "Promoters Responsive to DNA Bending: a Common Theme in Prokaryotic Gene Expression," *Microbiological Reviews* 58:268–290 (1994).

Rice et al., "Crystal Structure of an IHF–DNA Complex: A Protein–Induced DNA U–Turn," *Cell* 87:1295–1306 (1996).

Sambrook and Maniatis., *Molecular Cloning: A Laboratory Manual, 2$^{nd}$ Edition,* Cold Spring Harbor Laboratory Press (1989) (Table of Contents—All Three vols.).

Sarma, eds., "The Origins of the DNA Binding Affinity and Specificity of Minor Groove Directed ligands: Correlations of Thermodynamic and Structural Data," *Structure and Expression vol. 2: DNA and its Drug Complexes,* pp. 273–290.

Sluka et al., "Importance of Minor–Groove Contacts for Recognition of DNA by the Binding Domain of Hin Recombinase," *Biochemistry* 29:6551–6561 (1990).

Steitz, "Structural studies of protein–nucleic acid interaction: the sources of sequence–specific binding," *Quart. Rev. Biophys.* 23:205–280 (1990).

Strauss et al., "DNA Bending by Asymmetric Phosphate Neutralization," *Science* 266:1829–1834 (1994).

Swalley et al., "Discrimination of 5'–GGGG–3', 5'–GCGC–3', and 5'–GGCC–3' Sequences in the Minor Groove of DNA by Eight–Ring Hairpin Polyamides," *J. Am. Chem. Soc.* 119:6953–6961 (1997).

Thuong et al., "Sequence–Specific Recognition and Modification of Double–Helical DNA by Oligonucleotides," *Angew. Chem. Int. Ed. Engl.* 32:666–690 (1993).

Trauger et al., "Recognition of DNA by designed ligands at subnanomolar concentrations," *Nature* 382:559–56 (1996).

Turner et al., "Recognition of Seven Base Pair Sequences in the Minor Groove of DNA by Ten–Ring Pyrrole–Imidazole Polyamide Hairpins," *J. Am. Chem. Soc.* 119:7636–7644 (1997).

Wade et al., "Binding Affinities of Synthetic Peptides, Pyridine–2–carboxamidonetropsin and 1–Methylimidazole–2–carboxamidonetropsin, That Form 2:1 Complexes in the Minor Groove of Double–Helical DNA," *Biochemistry* 32:11385–11389 (1993).

Wade et al., "Design of Peptides That Bind in the Minor Groove of DNA at 5'–(A,T)G(A,T)C(A,T)–3' Sequences by a Dimeric Side–by–Side Motif," *J. Am. Chem. Soc.* 114:8783–8794 (1992).

White et al., "Effects of the A.T/T.A Degeneracy of Pyrrole–Imidazole Polyamide Recognition in the Minor Groove of DNA," *Biochemistry* 35:12532–12537 (1996).

White et al., "On the pairing rules for recognition in the minor groove of DNA by pyrrole–imidazole polyamides." *Chemistry & Biology* 4(8):569–578 (1997).

White et al., "Orientation Preferences of Pyrrole–Imidazole Polyamides in the Minor Groove of DNA," *J. Am. Chem. Soc.* 119:8756–8765 (1997).

Kopka, et al., "The molecular origin of DNA–drug specificity in netropsin and distamycin," *Proc. Natl. Acad. Sci. USA* 82:1376–1380 (Mar. 1985).

Lukhtanov, et al., "Minor groove DNA alkylation directed by major groove triplex forming oligodeoxyribonucleotides," *Nucleic Acids Research* 25(24): 5077–5084 (1997).

Parks, et al., Simultaneous Binding of a Polyamide Dimer and an Oligonucleotide in the Minor and Major Grooves of DNA, *Bioorganic & Medicinal Chemistry* 4(7): 1045–1050 (1996).

Pelton, et al., "Binding Modes of Distamycin A with d(CGCAAATTTGCG)$_2$ Determined by Two–Dimensional NMR," *J. Am. Chem. Soc.* 112:1393–1399 (1990).

Wiederholt, et al., "Oligonucleotides Tethering Hoechst 33258 Derivatives: Effect of the Conjugation Site on Duplex Stabilization and Fluorescence," *Bioconjugate Chem.* 8:119–126 (1997).

* cited by examiner

D.

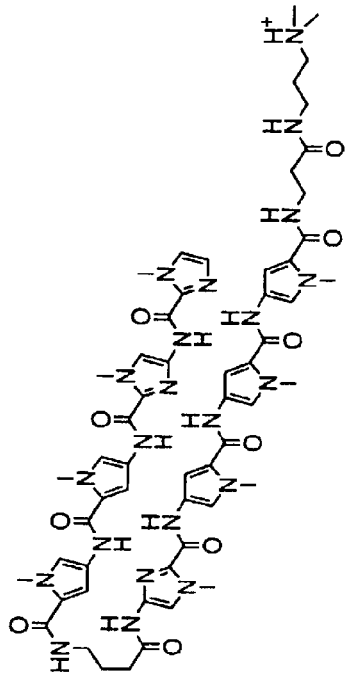
FIG. 2A (1) ImPyPyPy-γ-PyPyPyPy-β-Dp
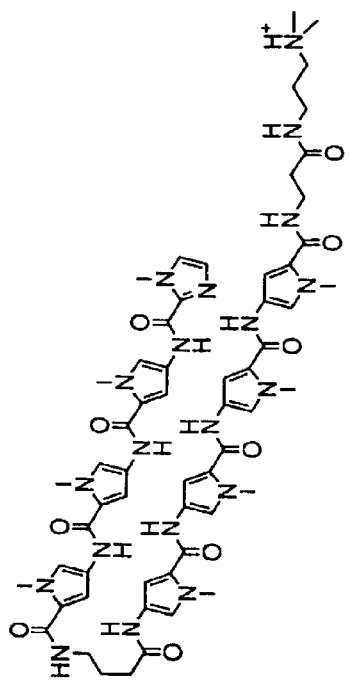
FIG. 2C (3) ImPyPyPy-γ-PyPyPyPy-β-RPR
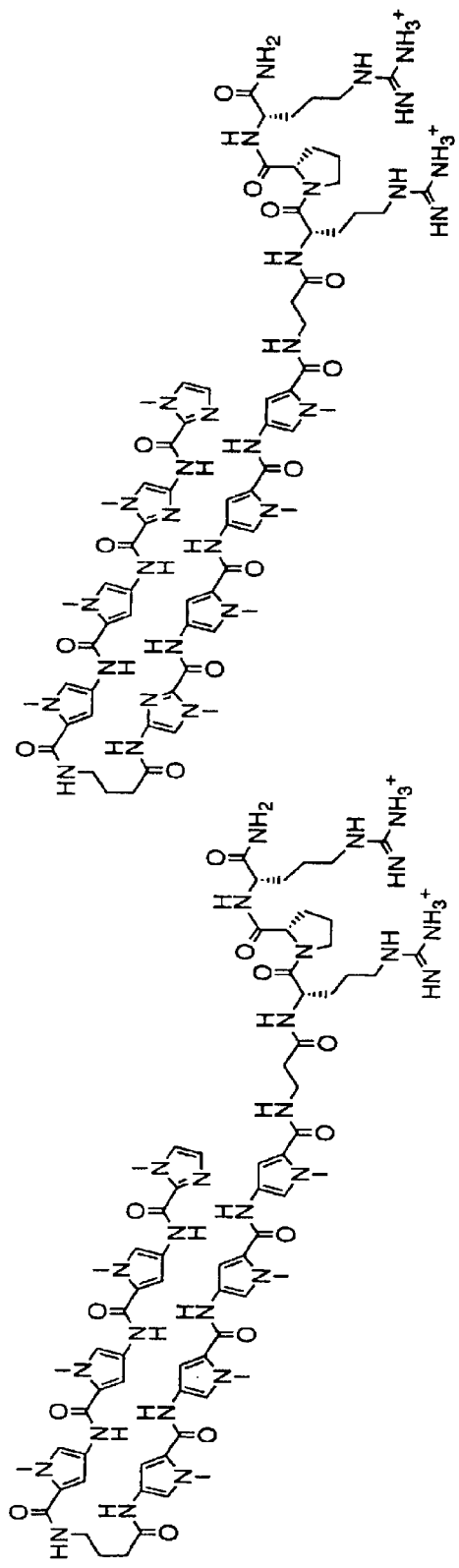
FIG. 2B (2) ImImPyPy-γ-ImPyPyPy-β-Dp
FIG. 2D (4) ImImPyPy-γ-ImPyPyPy-β-RPR ImImPyPy-γ-ImPyPyPy-β-RPR (4)

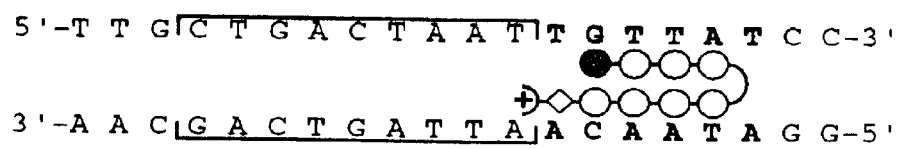
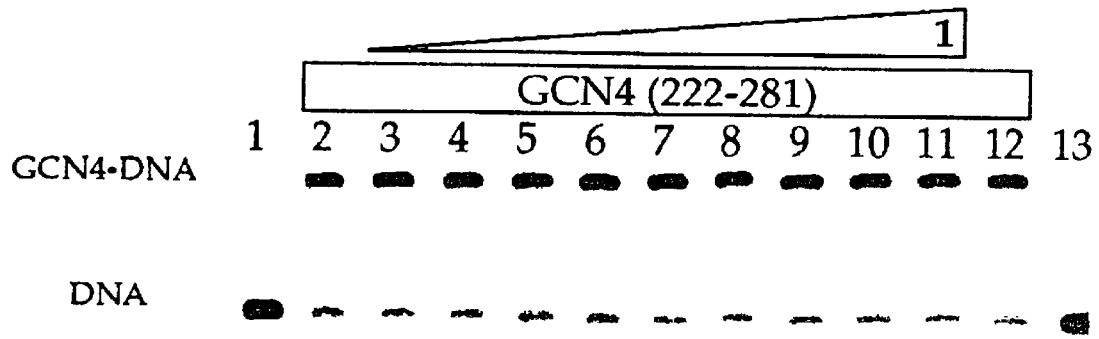
FIG. 5A
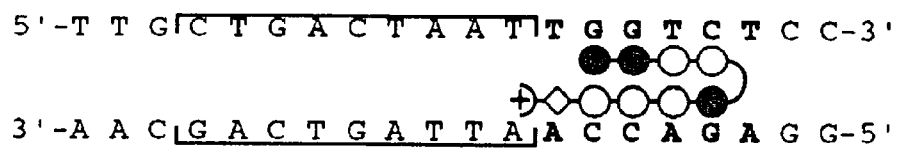
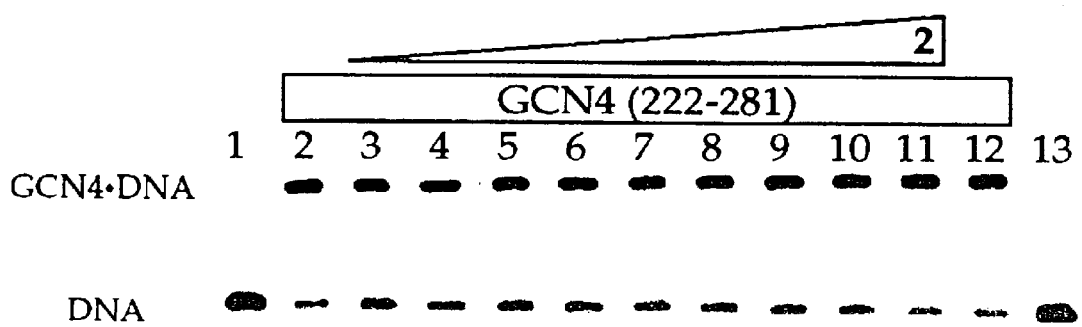
FIG. 5B

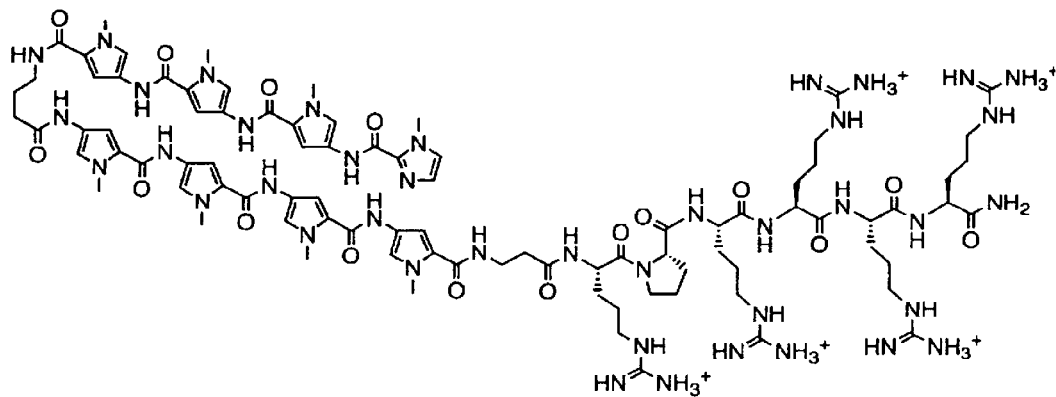
(5) ImPyPyPy-γ-PyPyPyPy-β-RPRRRR
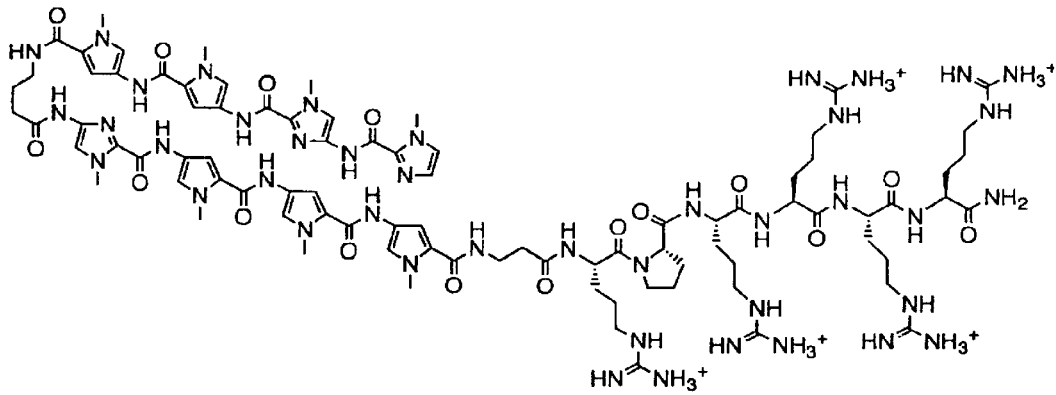
(6) ImImPyPy-γ-ImPyPyPy-β-RPRRRR
FIG. 6

ImPyPyPy-γ-PyPyPyPy-X

| Polyamide | X = | | Inhibition |
|---|---|---|---|
| 1 | | β-Dp | − |
| 3 | | β-RPR | ++ |
| 7 | | β-R | − |
| 8 | | β-RP | − |
| 9 | | β-RGR | + |

(14) ImPyPyPy-γ-PyPyPyPy-C7-RPR

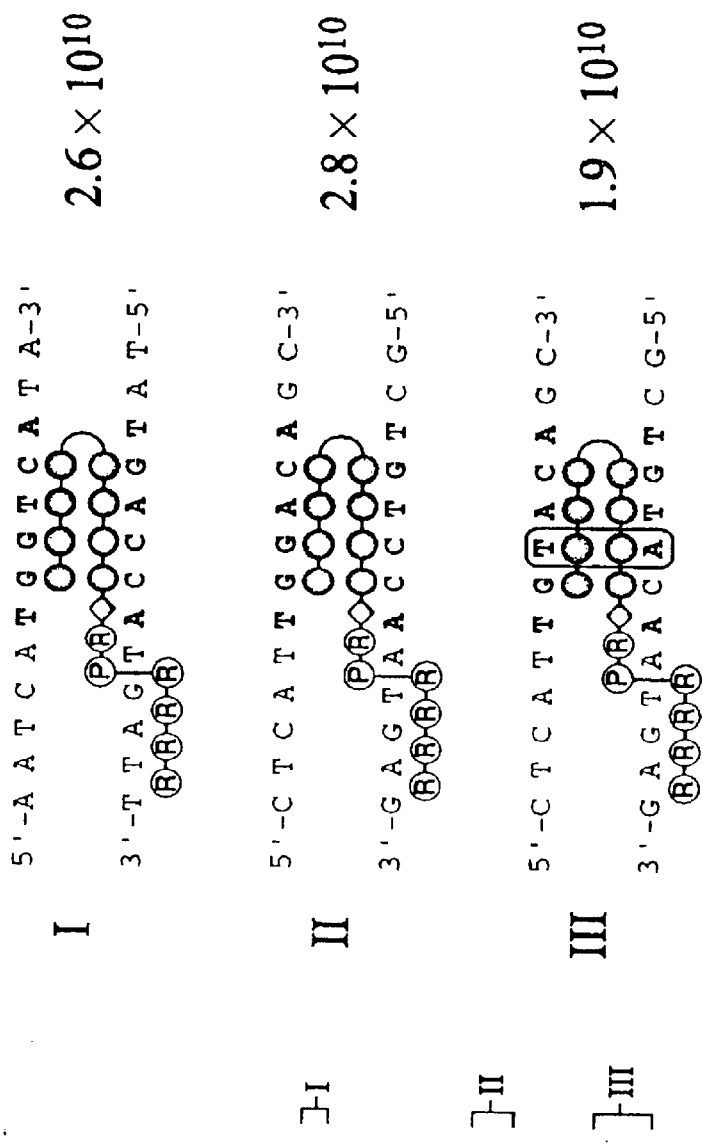
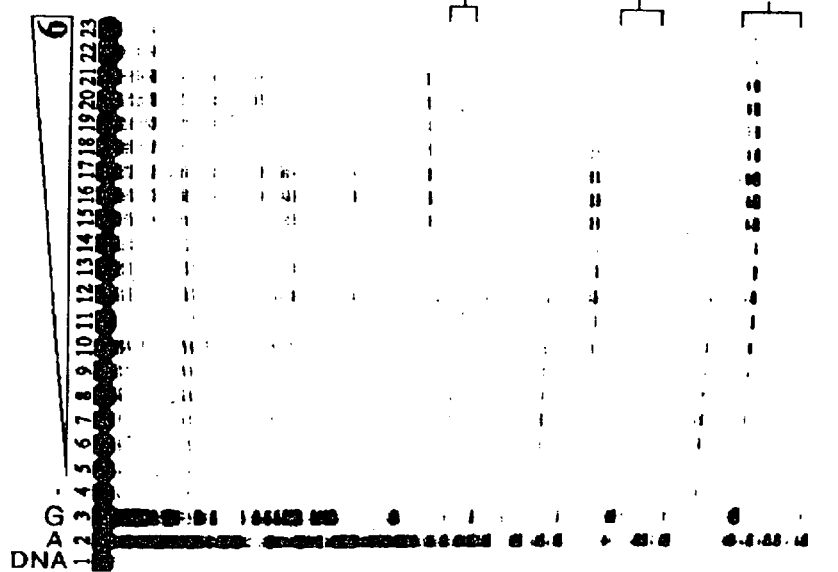
FIG. 10C

| oligonucleotide | 2 | 2 | 3 | 3 |
|---|---|---|---|---|
| polyamide | − | + | − | + |

| oligonucleotide | − | − | − | 2 | 2 | 2 |
|---|---|---|---|---|---|---|
| polyamide | − | 1 | 2 | − | 1 | 2 |

| oligonucleotide | − | − | − | 9 | 9 | 9 |
|---|---|---|---|---|---|---|
| polyamide | − | 1 | 2 | − | 1 | 2 | simultaneous addition | polyamide first | oligonucleotide first

INHIBITION OF MAJOR GROOVE DNA BINDING PROTEINS BY MODIFIED POLYAMIDES

CROSS-REFERENCE TO RELATED APPLICATIONS

This application claims priority to PCT/US98/02684 filed Feb. 13, 1998, and is a continuation-in-part of PCT/US97/03332 filed Feb. 20, 1997, Ser. No. 08/853,522 filed May 8, 1997 now U.S. Pat. No. 6,635,417, and PCT/US97/12722 filed Jul. 21, 1997 which are continuation-in-part applications of Ser. No. 08/837,524 filed Apr. 21, 1997, now U.S. Pat. No. 6,143,901 and Ser. No. 08/607,078 filed Feb. 26, 1996; provisional application 60/042,022, filed Apr. 16, 1997; provisional application 60/043,444 filed Apr. 8, 1997; PCT/US98/[MBHB 97,853]filed Jan. 21, 1998; PCT/US98/[MBHB 97,854]filed Jan. 29, 1998; and, PCT/US98/[MBHB98,016], filed Jan. 29, 1998. The specification of these applications are incorporated herein by reference.

The U.S. Government has certain rights to this invention pursuant to Grant Nos. GM 26453, 27681, and 47530 awarded by the National Institute of Health.

BACKGROUND OF THE INVENTION

1. Field of the Invention

This invention relates to polyamides which bind to predetermined sites of the minor groove of double-stranded DNA and have an α-amino acid domain ("positive patch") capable of inhibiting the activity of major groove DNA-binding proteins.

2. Background of the Invention

Polyamides containing N-methylpyrrole (Py) and N-methylimidazole (Im) amino acids bind to predetermined sequences in the minor groove of DNA with affinities and specificities comparable to naturally occurring DNA binding proteins (Trauger, et al. (1996) *Nature* 382, 559–561; Swalley, et al. (1997) *J. Am. Chem. Soc.* 119, 6953–6961; Turner, et al. (1997) *J. Am. Chem. Soc.* 119, 7636–7644). Sequence specificity is determined by a code of oriented side-by-side pairings of the Py and Im amino (Wade, et al. (1992) *J. Am. Chem. Soc.* 114, 8783–8794; Mrksich, et al. (1992) *Proc. Natl. Acad. Sci. U.S.A.* 89, 7586–7590; Wade, et al. (1993) *Biochemistry* 32, 11385–11389; Mrksich, et al. (1993) *J. Am. Chem. Soc.* 115, 2572–2576; White, et al. (1997) *Chem. Biol.* 4, 569–578; White, et al. (1997) *J. Am. Chem. Soc.* 119, 8756–8765). An Im/Py pairing targets a G·C base pair, while Py/Im pair recognizes C·G. The Py/Py pair is degenerate and targets both A·T and T·A base pairs (Pelton, et al. (1989) *Proc. Natl. Acad. Sci. USA* 86, 5723–5727; Chen, et al. (1994) *Nature Struct. Biol.* 1, 169–175; White, et al. (1996) *Biochemistry* 35, 12532–12537). The validity of the pairing rules for ligand design is supported by a variety of polyamide structural motifs which have been characterized by footprinting, affinity cleaving, 2-D NMR, and x-ray methods. The Py/Py pair is degenerate and targets both A·T and T·A base pairs. Polyamides have been found to be cell permeable and to inhibit transcription factor binding and expression of a designated gene (Gottesfeld, et al. (1997) *Nature* 387, 202–205; Nealy, et al. (1997) *J. Mol. Biol.* in press). Py/Im polyamides offer a potentially general approach for gene regulation, provided that efficient inhibition of DNA-binding can be achieved for a variety of transcription factors.

Several approaches for the development of synthetic ligands which interfere with protein-DNA recognition have been reported. Oligodeoxyribonucleotides which recognize the major groove of double-helical DNA via triple-helix formation bind to a broad range of sequences with high affinity and specificity (Moser, et al. (1987) *Science* 238, 645–650; Thuong, et al. (1993) *Angew. Chem. Int. Ed. Engl.* 32, 666–690). Although oligonucleotides and their analogs have been shown to disrupt protein-DNA binding (Maher, et al. (1992) *Biochemistry* 31, 70–81; Duval-Valentin, et al. (1992) *Proc. Natl. Acad. Sci. U.S.A.* 89, 504–508; Nielsen, P. E. (1997) *Chem. Eur. J.* 3, 505–508), the triple-helix approach is limited to purine tracts and suffers from poor cellular uptake. There are a few examples of carbohydrate-based ligands which interfere with protein-DNA recognition, but oligosaccharides cannot currently recognize a broad range of DNA sequences (Ho, et al. (1994) *Proc. Natl. Acad. Sci. USA* 91, 9203–9207; Liu, et al. (1996) *Proc. Natl. Acad. Sci. USA* 93, 940–944). Analogs of distamycin (PyPyPy) appended with multiple cationic substituents have been found to inhibit protein binding. Rational design of tripyrrole peptides that complex with DNA by both selective minor-groove binding and electrostatic interaction with the phosphate backbone. (Bruice (1992) *Proc. Natl. Acad. Sci. USA* 89, 1700–1704; Chiang, et al. (1997) *Proc. Natl. Acad. Sci. USA* 94, 2811–2816; Bruice, et al. (1997) *Bioorg. Med. Chem.* 5, 685–692). Based on these encouraging results, we wished to identify similar charged residues which could be appended to a Py/Im polyamide via linear solid phase synthesis and would not compromise polyamide binding specificity.

Proteins use a diverse structural library to recognize their target sequences (Steitz, T. A. (1990) *Quart. Rev. Biophys.* 23, 205–280). Proteins such as TBP bind exclusively in the minor groove (Kim, et al. (1993) *Nature* 365, 512–520), others, such as GCN4 Oakley, M. G. & Dervan, P. B. (1990) Structural motif of the GCN4 DNA binding domain characterized by affinity cleaving (Oakley, et al. (1990) *Science* 248, 847–850; Ellenberger, et al. (1992) *Cell* 71, 1223–1237; König, et al. (1993) *J. Mol. Biol.* 233, 139–154), bind exclusively in the major groove, and certain proteins such as Hin recombinase recognize both grooves (Sluka, et al. (1990) *Biochemistry* 29, 6551–6561; Feng, et al. (1994) *Science* 263, 348–355). Polyamides have been found to interfere with protein-DNA recognition in cases where contacts in the minor groove are important for protein-DNA binding affinity. For example, within the nine zinc-finger protein TFIIIA, fingers 4 and 6 bind in or across the minor groove and are required for high affinity binding ($K_a=5\times10^9$ $M^{-1}$). An eight-ring hairpin polyamide ($K_a=3\times10^{10}$ $M^{-1}$) targeted to the minor groove contact region of finger 4 has been recently found to efficiently inhibit protein binding.

X-Ray crystallography studies reveal that DNA bound by a 4-ring homodimeric polyamide is unaltered from its natural B-form structure, with all polyamide/DNA contacts confined to the minor groove (Kielkopf, et al. *Nature Struct. Biol.*, in press). Polyamides have been shown to bind simultaneously with ligands that exclusively occupy the major groove (Oakley, et al. (1992). *Biochemistry* 31, 10969–10975; Park, et al. (1992) *Proc. Natl. Acad. Sci. USA* 89, 6653–6657). For example, an 8-ring hairpin polyamide and a recombinant protein containing only the three amino-terminal zinc fingers of TFIIIA which are in the major groove were found to co-occupy the TFIIIA binding site. Similarly, the three-ring homodimer ImPyPy bound simultaneously with the bZIP protein GCN4 (226–281).

Intrinsic DNA curvature and protein induced DNA bending are also involved in the regulation of gene transcription, replication initiation, and other processes (Perez-Martin, J., et al. (1994) *Microbiological Reviews* 58, 268–290; Polaczek, et al. (1997), submitted). DNA is an inherently flexible polymer and neutral backbone analogs of DNA curve, where rigidity is maintained in natural DNA by coulombic repulsion between phosphates on the same strand Strass, et al. (1994) *Science* 266, 1829–1834; Manning, G. S. (1983) *Biopolymers* 22, 689–729). Sequence-dependent curvature of DNA is caused both by differential solvation in the minor groove and differential base stacking leading to alteration of roll and tilt values (Dlakic, et a (1996) *J. Biological Chemistry* 271, 17911–17919; Bolshoy, et al. (1991) *Proc. Natl. Acad. Sci., USA* 88, 2312–2316).

Proteins and other ligands that bend DNA alter the stacking of the bases by intercalation of hydrophobic groups, alter the effective Debye length of the surface through charge screening, or bend through energetic compensation for tight binding events. An example of a protein that seems to work through all three mechanisms in bending DNA >160 degrees is integration host factor (IHF) (Rice, et al. (1996) *Cell* 87,1295–1306). Previously, it has been shown that artificial sequence specific DNA bending ligands can be designed that utilize bidentate tight binding third strand oligonucleotides to constrict the intervening duplex and bend DNA (Liberles, et al. (1996) *Proc. Natl. Acad. Sci., USA* 93, 9510–4; Akiyama, et al. (1996) *Proc. Natl. Acad. Sci., USA* 93, 1212212127; Akiyama, et al. (1996) *J. Biological Chemistry* 271, 29126–29135; Akiyama, et al. (1997) *Biochemistry* 36,2307–2315).

Compounds that bind in the minor groove such as distamycin and DAPI have been shown to alter DNA rigidity (Larsson, et al. (1996) *J. Physical Chemistry* 100, 3252–3263; McCarthy, et al. (1991) *Nucleic Acids Research* 19, 3421–9; Barcelo, et al. (1991) *Biochemistry* 30, 4863–73.). While such compounds form few specific contacts and binding is dominated by the positive charge, polyamide analogs of distamycin have been designed that form specific high affinity structures with DNA in the minor groove. In such compounds, sequence specificity is determined by the sequence of side-by-side amino acid pairings, where imidazole (Im) opposite pyrrole (Py) recognizes a GC base pair, Py-Im recognizes CG, Py-Py is degenerate for AT or TA, while Im-Im pairing is disfavored (Wade, et al. (1992) *J. Am. Chem. Soc.* 114, 87838794; Mrksich, et al. (1992) *Proc. Natl. Acad. Sci., USA* 89,7586–7590; Wade, et al. (1993) *Biochemistry* 32, 1138511389; Pelton, et al. (1989) *Proc. Natl. Acad. Sci., USA* 86, 57235727; Pelton, et al. (1990) *J. Am. Chem. Soc.* 112,1393–1399). This recognition motif generality has been demonstrated for a large number of sequences and is directly supported by NMR data (Mrksich, et al. (1993) *J. Am. Chem. Soc.* 115, 2572–2576; Geierstanger, et al. (1994) *Biochemistry* 33, 3055–3062; Geierstanger, et al. (1993) *J. Am. Chem. Soc.* 115, 4474–4482; Geierstanger, et al. (1994) *Science* 266, 646–650; Mrksich, et al. (1995) *J. Am. Chem. Soc.* 117, 3325–3332; Mrksich, et al. (1993) *J. Am. Chem. Soc.* 115, 9892–9899; Dwyer, et al. (1993) *J. Am. Chem. Soc.* 115, 9900–9906; Mrksich, et al. (1994) *J. Am. Chem. Soc.* 116, 3663–3664; Mrksich, et al. (1994) *J. Am. Chem. Soc.* 116, 79837988; Chen, et al. (1994) *J. Am. Chem. Soc.* 116, 6995–7005; Cho, et al. (1995) *Proc. Natl. Acad. Sci., USA* 92, 10389–10392).

BRIEF DESCRIPTION OF THE FIGURES

FIG. 2. Schematic models of Arg-Pro-Arg polyamides.

FIG. 6. GCN4 gel mobility shift experiments.

FIG. 18. MPE and DNase I footprinting analysis of oligonucleotide2 on a $3'^{32}P$ end-labeled restriction fragment generated with EcoRI and PvuII.

SUMMARY OF THE INVENTION

Figure 1A:
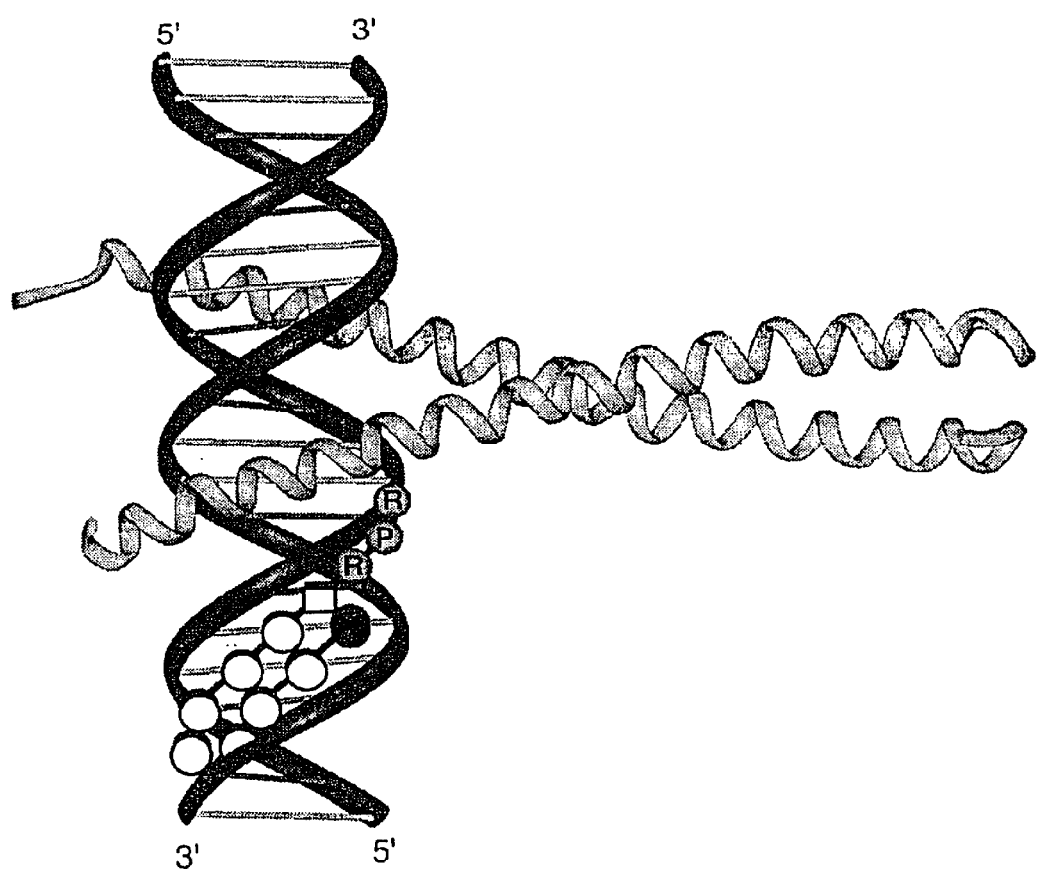
FIG. 1. Schematic models of polyamides targeted to GCN4 binding site.
Figure 1B:
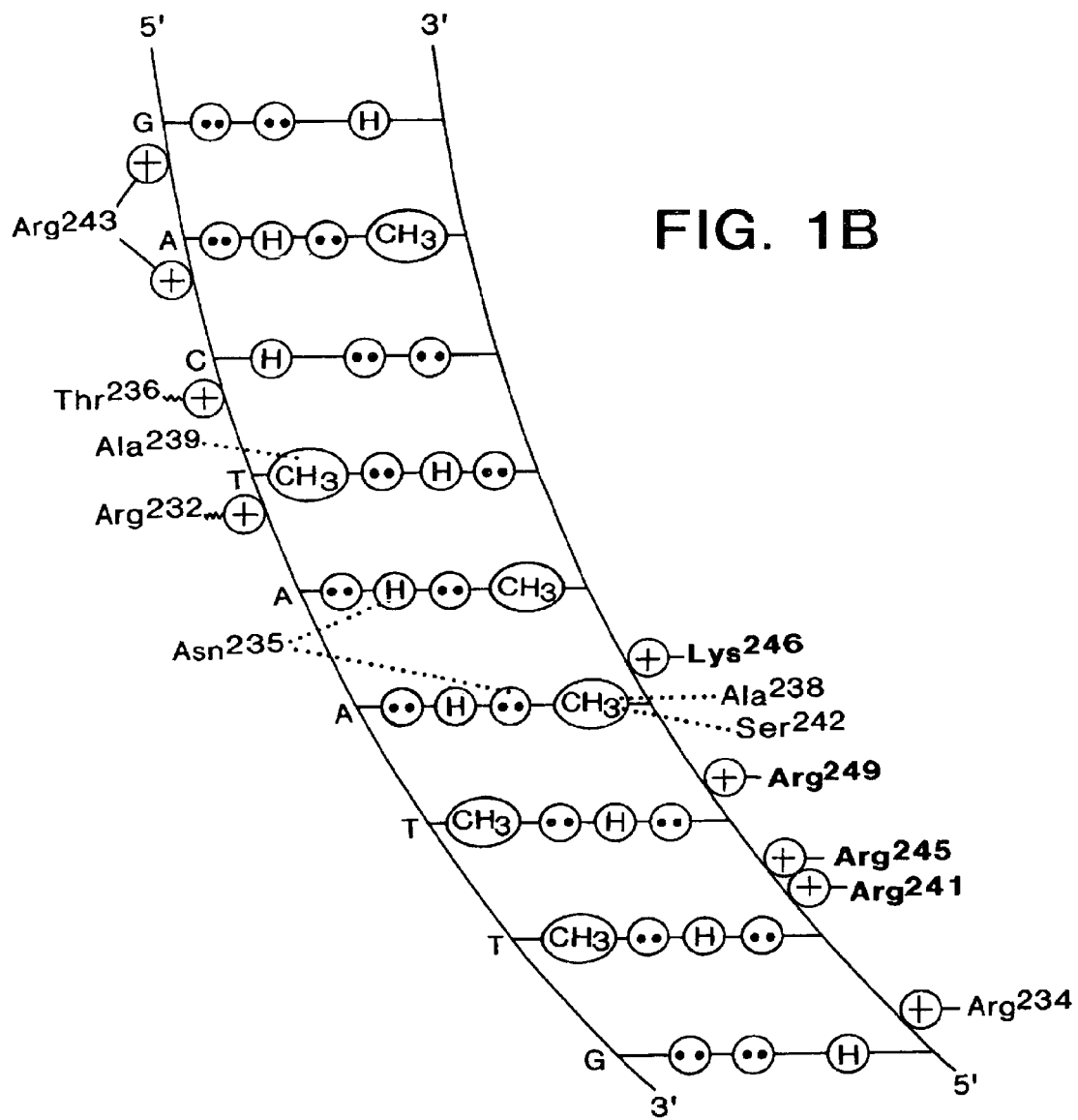
Figure 1C:
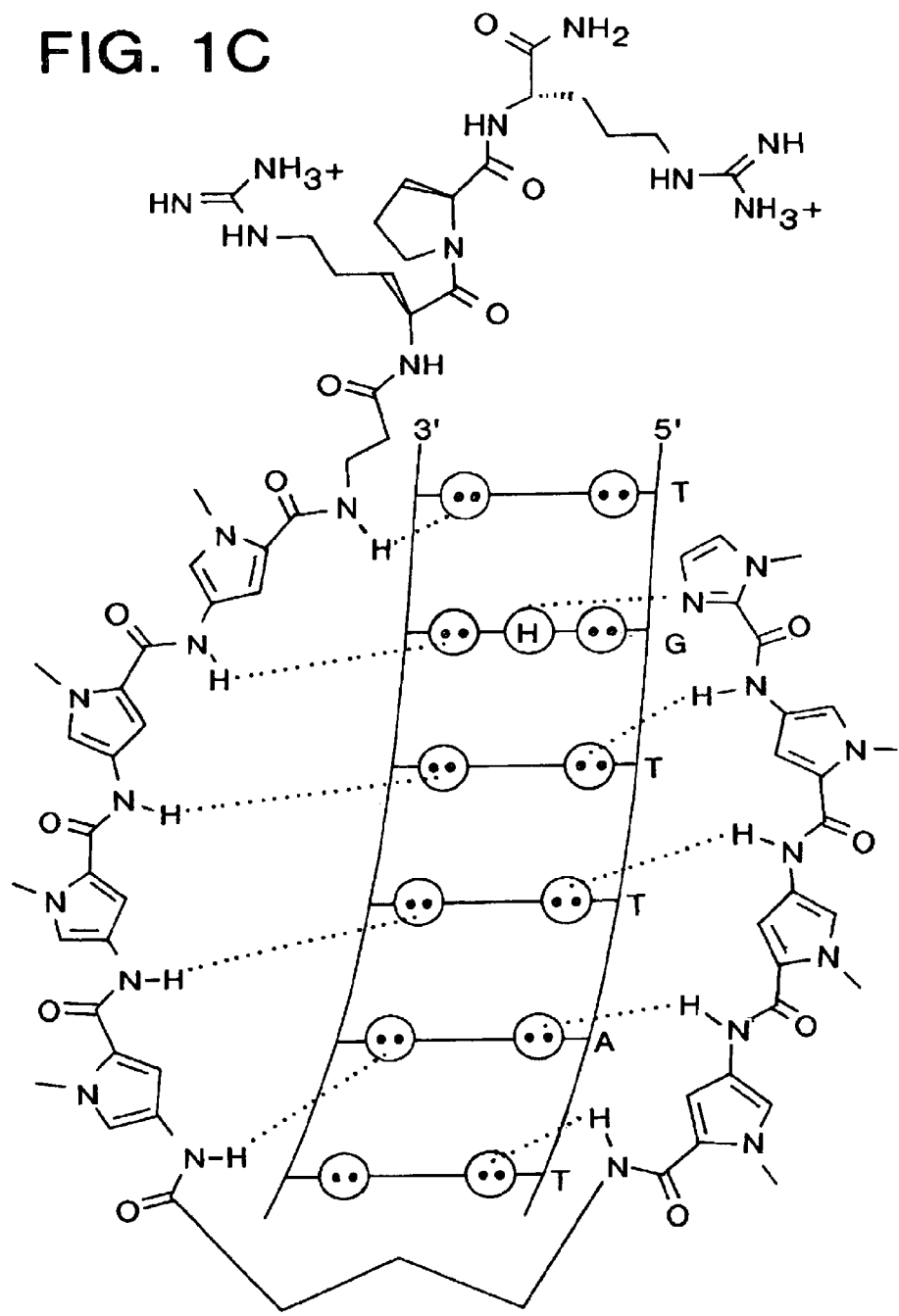
Figure 1D:
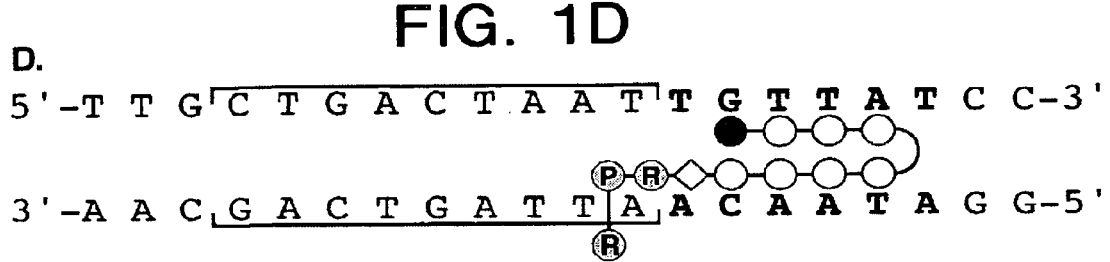

This invention provides improved polyamides comprising a positive patch that, upon binding of the polyamide to the minor groove of a DNA molecule, is able to contact nucleotides in the major groove of a DNA molecule. The positive patch may comprise any chemical moiety that delivers a charge to the DNA molecule. The invention further comprises polyamides comprising having the ability to alter the conformation of a DNA molecule such that the function of a conformation-dependent DNA binding protein is inhibited. As such, the polyamides inhibit gene expression by binding the minor groove DNA sequence and displacing or preventing the binding or function of DNA-binding proteins such as transcription factors.

DETAILED DESCRIPTION

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, Vol. 185, Academic Press, San Diego, Calif. (1991); "Guide to Protein Purification" in Deutshcer, M. P., ed., *Methods in Enzymology*, Academic Press, San Diego, Calif. (1989); Innis, et al., *PCR Protocols: A Guide to Methods and Applications*, Academic Press, San Diego, Calif. (1990); Freshney, R. I., *Culture of Animal Cells: A Manual of Basic Technique*, 2$^{nd}$ Ed., Alan Liss, Inc. New York, N.Y. (1987); Murray, E. J., ed., *Gene Transfer and Expression Protocols*, pp. 109–128, The Humana Press Inc., Clifton, N.J. and Lewin, B., *Genes VI*, Oxford University Press, New York (1997).

For the purposes of this application, a promoter is a regulatory sequence of DNA that is involved in the binding of RNA polymerase to initiate transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream ("5' to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogeneous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a polyamide to prevent binding of a factor to a silencer regulatory sequence or indirectly, by using a polyamide to block transcription of a factor to a silencer regulatory sequence.

It is to be understood that the polyamides of this invention bind to double stranded DNA in a sequence specific manner. The function of a segment of DNA of a given sequence, such as 5'-TATAAA-3', depends on its position relative to other functional regions in the DNA sequence. In this case, if the sequence 5'-TATAAA-3' on the sense strand of DNA is positioned about 30 base pairs upstream of the transcription start site, the sequence forms part of the promoter region (Lewin, *Genes VI*, pp. 831–835). On the other hand, if the sequence 5'-TATAAA-3' is downstream of the transcription start site in a coding region and in proper register with the reading frame, the sequence encodes the tyrosyl and lysyl amino acid residues (Lewin, *Genes VI*, pp. 213–215).

While not being held to one hypothesis, it is believed that the binding of the polyamides of this invention modulate gene expression by altering the binding of DNA binding proteins, such as RNA polymerase, transcription factors, TBF, TFIIIB and other proteins. The effect on gene expression of polyamide binding to a segment of double stranded DNA is believed to be related to the function, e.g., promoter, of that segment of DNA.

It is to be understood by one skilled in the art that the improved polyamides of the present invention may bind to any of the above-described DNA sequences or any other sequence having a desired effect upon expression of a gene. In addition, U.S. Pat. No. 5,578,444 describes numerous promoter targeting sequences from which base pair sequences for targeting an improved polyamide of the present invention may be identified.

It is generally understood by those skilled in the art that the basic structure of DNA in a living cell includes both major and a minor groove. For the purposes of describing the present invention, the minor groove is the narrow groove of DNA and the major groove is the deep groove of DNA as illustrated in common molecular biology references such as Lewin, B., *Genes VI*, Oxford University Press, New York (1997).

It is further understood by those skilled in the art that a DNA binding protein is a protein capable of making contact with a DNA molecule, generally in the major groove, through hydrogen bonds, ionic bonds and/or hydrophobic interactions as illustrated in common molecular biology references such as Lewin, supra, or Alberts, et al., Eds., *Molecular Biology of the Cell, 3$^{rd}$*, Ed., Garland Publishing, Inc., New York, 1994. Preferably, a DNA-binding protein is one that affects gene expression following binding to a DNA molecule.

Several basic motifs of DNA-binding proteins are known to those skilled in the art. One such conformation is the helix-turn-helix motif, which includes a specific subclass known as homeodomain proteins. Other common motifs include the zinc finger motif, the leucine zipper motif, and the helix-loop-helix motif. A DNA-binding protein of this application may maintain any of the above-described motifs or any other motif that provides a protein with the ability to bind DNA and affect gene expression.

To affect gene expression in a cell which may include causing an increase or a decrease in gene expression, a effective quantity of one or more polyamide is contacted with the cell and internalized by the cell. The cell may be contacted in vivo or in vitro. Effective extracellular concentrations of polyamides that can modulate gene expression range from about 10 nanomolar to about 1 micromolar. Gottesfeld, J. M., et al., *Nature* 387 202–205 (1997). To determine effective amounts and concentrations of polyamides in vitro, a suitable number of cells is plated on tissue culture plates and various quantities of one or more polyamide are added to separate wells. Gene expression following exposure to a polyamide can be monitored in the cells or medium by detecting the amount of the protein gene product present as determined by various techniques utilizing specific antibodies, including ELISA and western blot. Alternatively, gene expression following exposure to a polyamide can be monitored by detecting the amount of messenger RNA present as determined by various techniques, including northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a polyamide can be monitored by detecting the amount of the protein gene product present as determined by various techniques utilizing specific antibodies, including ELISA and western blot. Alternatively, gene expression following exposure to a polyamide can be monitored by detecting the amount of messenger RNA present as determined by various techniques, including northern blot and RT-PCR.

The polyamides of this invention may be formulated into diagnostic and therapeutic compositions for in vivo or in vitro use. Representative methods of formulation may be found in *Remington: The Science and Practice of Pharmacy*, 19th ed., Mack Publishing Co., Easton, Pa. (1995).

For in vivo use, the polyamides may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected compound, the intended use, the nature and severity of the condition being treated or diagnosed, the age, weight, gender, physical condition and mental acuity of the intended recipient as well as the route of administration. Such considerations are within the purview of the skilled artisan. Thus, the dosage regimen may vary widely, but can be determined routinely using standard methods.

Polyamides of the present invention are also useful for detecting the presence of double stranded DNA of a specific sequence for diagnostic or preparative purposes. The sample containing the double stranded DNA can be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

The design of bifunctional sequence specific DNA binding molecules requires the integration of two separate entities: recognition and functional activity. Polyamides that specifically bind with subnanomolar affinity to the minor groove of a predetermined sequence of double stranded DNA are linked to a functional molecule, providing the corresponding bifunctional conjugates useful in molecular biology, genomic sequencing, and human medicine. Polyamides of this invention can be conjugated to a variety of functional molecules, which can be independently chosen from but is not limited to arylboronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, (+)-α-tocopheral, EDTA, methidium, acridine, Ni(II).Gly-Gly-His, thiazole orange (TO), Dansyl, pyrene, N-bromoacetamide, and gold particles. Such bifunctional polyamides are useful for DNA affinity capture, covalent DNA modification, oxidative DNA cleavage, DNA photocleavage. Such bifunctional polyamides are useful for DNA detection by providing a polyamide linked to a detectable label. Detailed instructions for synthesis of such bifunctional polyamides can be found in copending U.S. provisional application No. 60/043,444, the teachings of which are incorporated by reference.

DNA complexed to a labeled polyamide can then be determined using the appropriate detection system as is well known to one skilled in the art. For example, DNA associated with a polyamide linked to biotin can be detected by a streptavidin/alkaline phosphatase system.

The present invention also describes a diagnostic system, preferably in kit form, for assaying for the presence of the double stranded DNA sequence bound by the polyamide of this invention in a body sample, such brain tissue, cell suspensions or tissue sections, or body fluid samples such as CSF, blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific polyamide as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microtiter plate well to which microgram quantities of a contemplated polyamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

Trauger, et al. (*Nature,* 382: 559–561) and Swalley, et al. (*J. Am. Chem. Soc.* 119: 6953–6961) have described recognition of DNA by certain polyamides at subnanomolar concentrations. Pairing specific carboxyamide groups allows for recognition of specific DNA sequences (Swalley, et al. supra). Polyamides comprising Hp, Im, and Py provide for coded targeting of pre-determined DNA sequences with high affinity and specificity. Hp, Im, and Py polyamides may be combined to form Im/Py, Py/Im, Hp/Py, and Py/Hp binding pairs which complement the four Watson-Crick base pairs A, C, G, and T. Table 1 illustrates such pairings.

TABLE 1

Pairing Codes for Base Pair Recognition*

| Pair | G·C | C·G | T·A | A·T |
|---|---|---|---|---|
| Im/Py | + | − | − | − |
| Py/Im | − | + | − | − |
| Hp/Py | − | − | + | − |
| Py/Hp | − | − | − | + |

*favored (+), disfavored (−)

Three-, four-, five- or six-ring improved polyamides of the present invention are covalently coupled to form six-, eight-, ten- or twelve-ring structures, respectively, that bind specifically to four or six base pair targets, respectively, at subnanomolar concentrations. As such, the improved polyamides of the present invention may be directed to any DNA sequence comprised of A, C, G, or T.

The instant invention provides polyamides having the ability to interfere with gene expression by altering the topology of a DNA molecule physically or by altering the chemical environment of the DNA molecule. By altering the topology of a DNA molecule, it is possible to inhibit the function of DNA-binding proteins that are dependent on DNA conformation for binding. The inclusion of a positive patch in a polyamide allows for alteration of the chemical environment surrounding the DNA molecule and serves to inhibit binding or function of DNA-binding proteins that bind the major groove of a DNA molecule.

Transcription and replication of DNA is dependent upon intrinsic DNA curvature and protein-induced DNA bending. Previously, sequence-specific DNA bending ligands have been designed to bind two noncontiguous target sites in the major groove and induce a bend in the DNA (Liberles, D. A. & Dervan, P. B. (1996) Proc. Natl. Acad. Sci., USA 93, 95104). This bend was shown to be dependent upon the linker length connecting the two sites. The present invention comprises sequence-specific polyamides targeted to the minor groove of the double helical linker region not overlapping either triple helical region, are capable of inhibiting bidentate third strand oligonucleotide binding. This inhibition through rigidification of the duplex is dependent upon the bend angle of the DNA, but is independent of the order of addition of bending and straightening ligands. As such, polyamides may be useful for displacing DNA bending transcription factors in cells.

It has been demonstrated that artificial sequence-specific DNA bending ligands can be designed that utilize bidentate tight binding third strand oligonucleotides to constrict the intervening duplex and bend DNA (Liberles, et al.). (1996) Proc. Natl. Acad. Sci., USA 93, 9510–4; Akiyama, et al. (1996) Proc. Natl. Acad. Sci., USA 93, 12122–12127; Akiyama, et al. (1996) J. Biological Chemistry 271, 29126–29135; Akiyama, et al. (1997) Biochemistry 36, 2307–2315). Presented herein is a mechanism of action by which certain improved polyamides affect DNA conformation, thus inhibiting the function of DNA-binding proteins that are dependent upon the conformation of DNA for binding. While compounds such as DAPI form a few specific contacts and binding is dominated by the positive charge of the compound, polyamide analogs of distamycin have been designed that form specific high affinity structures with DNA in the minor groove. Provided herein are polyamides having the ability to displace a DNA bending by rigidification of a bent region not contacted by the ligand. A polyamide of the present invention may be utilized to "straighten", defined herein as altering the conformation of a DNA molecule such that a conformationally-dependent DNA-binding protein is unable to bind to the DNA or function properly, DNA molecules of widely varying sequence.

The negatively charged DNA phosphate backbone provides a target for ligands designed to disrupt the unique microenvironment representing a protein binding site on the DNA double helix. The present invention comprises improved polyamides having a positive patch. Preferably, the positive patch contacts the phosphate backbone and disrupts the microenvironment, thereby preventing the binding and/or function of proteins that bind the DNA major groove. Polyamides that deliver a positive patch to the DNA backbone most likely destabilize the contacts between the protein side chains and the phosphate residues, and thereby inhibit protein binding (Bruice, et al. (1992). Proc. Natl. Acad. Sci. USA 89, 1700–1704; Chiang, et al. (1997). Proc. Natl. Acad. Sci. USA 94, 2811–2816; Bruice, et al. (1997). Bioorg. Med. Chem. 5, 685–692) (FIG. 1).

Figure 12:
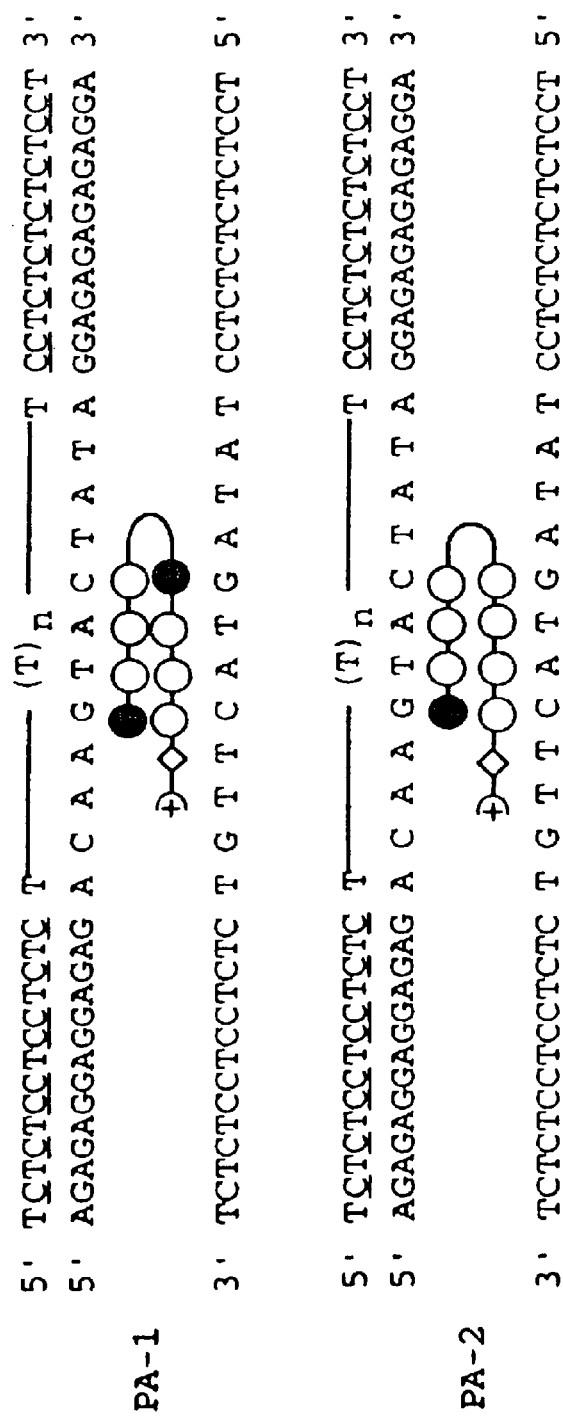
FIG. 12. Structural requirements for GCN4 binding.

The positive patch comprises any chemical moiety that is capable of delivering a charge to the chemical environment of the DNA molecule. The positive patch comprises a charged group placed on the C-terminus, N-terminus, N-methyl group or other modifiable position of the polyamide. Preferably, the charged group comprises any amino acid having a net charge of at least +1. More preferably, the charged group is a primary, secondary, tertiary, quarternary amino group or a guanidinium or amidinium group. In one embodiment, the positive patch comprises an amino acid residue having a net positive charge joined to the C-terminus of a polyamide such that the polyamide has the ability to displace or prevent the binding of a DNA-binding protein to the major groove of a DNA molecule (FIG. 12).

It has been demonstrated that a variety of polyamide motifs co-occupy the DNA helix at sites both overlapping and adjacent to certain DNA-binding proteins, such as GCN4 (FIG. 1). Table 2 shows schematic models of polyamides targeted to the binding site of the bZIP transcriptional activator, GCN4: ImPyPy-Dp, ImPyPy-γ-ImPyPy-β-Dp, ImPyPyPy-γ-PyPyPyPy-β-Dp, and ImPyPy-γ-ImPyPy-β-PyPyPy-G-Dp. The nine-base pair (5'-CTGACTAAT-3') GCN4 binding site is indicated by brackets above and below the base pairs. Filled and unfilled circles represent imidazole (Im) and pyrrole (Py) polyamide rings, respectively. Diamonds and triangles represent β-alanine (β) and glycine (G), respectively. γ-Aminobutyric acid (γ) and dimethylaminopropylamide (Dp) are depicted as a curved line and a plus sign, respectively. Polyamide binding sites are shown in bold. Equilibrium association constants ($K_a$) for each polyamide binding to the indicated match site are shown at the right. Association constants were determined by DNase I footprinting; simultaneous binding was determined by gel mobility shift assay.

TABLE 2

Polyamide Motifs That Bind Simultaneously with Major Groove DNA-Binding Proteins

| Polyamide | Complex | $K_a$ (M$^{-1}$) |
|---|---|---|
| ImPyPy-Dp | 5'-T G C ⌈C T G A C T A A T⌉A G T -3'<br>●○○◈<br>◇○○●<br>3'-A C G⌊G A C T G A T T A⌋T C A -5' | 1 × 10$^5$ |
| ImPyPy-γ-ImPyPy-β-Dp | 5'-T G C ⌈C T G A C T A A T⌉A G T -3'<br>●○○◇◈<br>○○●<br>3'-A C G⌊G A C T G A T T A⌋T C A -5' | 1 × 10$^7$ |

TABLE 2-continued

Polyamide Motifs That Bind Simulataneously with Major Groove DNA-Binding Proteins

| Polyamide | Complex | $K_a$ (M$^{-1}$) |
|---|---|---|
| ImPyPyPy-γ-PyPyPyPy-β-Dp | 5'-G⌈C T G A C T A A T⌉T G T T A T C-3'<br>●○○○<br>▷◇◇○○○<br>3'-C⌊G A C T G A T T A⌋A C A A T A G-5' | $1 \times 10^9$ |
| ImPyPy-γ-ImPyPy-β-PyPyPy-G-Dp | 5'-T G C⌈C T G A C T A A T⌉A G T-3'<br>●○○◇◇○○○▷◁<br>○○●<br>3'-A C G⌊G A C T G A T T A⌋T C A-5' | $1 \times 10^{10}$ |

The improved polyamides of the present invention have at least three consecutive carboxamide pairings for binding DNA in the minor groove of a regulatory sequence of a duplex gene sequence, and a positive patch sequence for interference with DNA-binding protein function. The improved polyamides may further comprise a chiral hairpin turn having a stereochemical center substituted at the γ-position of the chiral hairpin turn of the molecule with the R-enantiomer of 2,4-diaminobutyric acid (H$_2$NHCHCH$_2$CHNH$_2$—COOH; "(R)$^{H_2N}$γ").

The present invention comprises improved polyamides having three or four-ring polyamide structures covalently coupled to form six-, eight-, ten- or twelve-ring hairpin structures, respectively, of the general structures I–VIII:

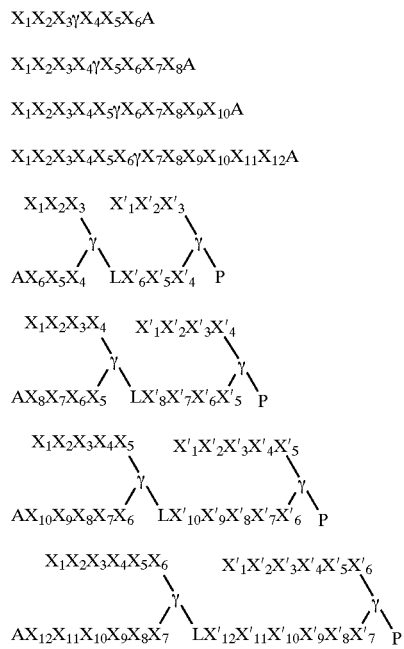

$$X_1X_2X_3\gamma X_4X_5X_6A \quad \text{I}$$

$$X_1X_2X_3X_4\gamma X_5X_6X_7X_8A \quad \text{II}$$

$$X_1X_2X_3X_4X_5\gamma X_6X_7X_8X_9X_{10}A \quad \text{III}$$

$$X_1X_2X_3X_4X_5X_6\gamma X_7X_8X_9X_{10}X_{11}X_{12}A \quad \text{IV}$$

V, VI, VII, VIII (hairpin structures as depicted)

where $X_{1-12}$ and $X'_{1-12}$ are independently an imidazole such as N-methylimidazole (Im), a pyrrole such as N-methylpyrrole (Py), or a hydroxypyrrole such as 3-hydroxy-N-methyl pyrrole (Hp). In addition, an improved polyamide of the present invention may further include a aliphatic amino acid such as β-alanine residue (β), an amide group such as dimethylaminopropylamide (Dp), an alcohol such as EtOH, an acid such as EDTA, or any derivative thereof may be joined to the β residue.

"A" represents a positive patch which comprises any chemical moiety that is capable of delivering a positive charge to the major groove of a DNA molecule. Preferably, the positive patch comprises a rigid group joined to a positively charged group. The rigid group positions the positively charged group such that contact with the major groove or the phosphate backbone of a DNA molecule is accomplished.

Preferably, the rigid group comprises one to ten amino acids. More preferably, the rigid group comprises one to eight amino acids. More preferably, the rigid group comprises one to six amino acids. More preferably, the rigid group comprises one to four amino acids. Most preferably, the rigid group comprises two amino acids. Of the most preferred rigid group, the first amino acid is positioned adjacent to the polyamide and may comprise arginine, proline, lysine, hydroxyproline, the corresponding L or D enantiomers thereof or a derivative thereof. Preferably, the first amino acid is arginine or lysine and most preferably the first amino acid is arginine. The second amino acid is positioned at the carboxy end of the first amino acid. Suitable second amino acids comprise proline, glycine, serine, threonine, leucine, isoleucine, valine, alanine, hydroxyproline the corresponding L or D enantiomers thereof or a derivative thereof. Preferably, the second amino acid is proline or glycine and most preferably the second amino acid is proline.

A suitable positively charged group comprises a synthetic or naturally occurring amino acid. Preferably, the positively charged group is a primary amino group, secondary amino group, tertiary amino group, quarternary amimo group, guanidinium group or amidinium group. It is preferred that the positively charged group is an amino acid bearing a net charge of at least +1. More preferably, the positively charged group is arginine, lysine, histidine or a derivative thereof. Most preferably, the positively charged group is arginine.

The positive patch may be joined to the polyamide using an "attachment" group. Preferably, the attachment group comprises an amino acid. More preferably, the attachement moiety is β-alanine, γ-aminobutyric acid, valeric acid, or any of the corresponding 2-amino derivatives of β-alanine, γ-aminobutyric acid, or valeric acid. Most preferably, the attachment group is β-alanine.

In addition, an improved polyamide of the present invention may further include a aliphatic amino acid such as β-alanine residue (β), an amide group such as dimethylaminopropylamide (Dp), an alcohol such as EtOH, an acid such as EDTA, or any derivative thereof may be joined to the β residue.

β-alanine may also be utilized in place of a pyrrole or hydroxypyrrole amino acid in Formulas I–VIII. The use of β-alanine in place of a pyrrole or hydroxypyrrole amino acid in the synthetic methods provides aromatic/aliphatic pairing (Im/β, β/Im, Py/β, and β/Py) and aliphatic/aliphatic pairing (β/β) substitution. Such substitutions may comprise those described in provisional application 60/042,022, incorporated herein by reference. The use of γ-aminobutyric acid, or a substituted γ-aminobutyric acid such as (R)-2,4 diaminobutyric acid, provides for preferred hairpin turns. Inclusion of the positive patch allows the polyamide to deliver a positive residue to the DNA backbone and interfere with protein-phosphate contacts. As such, the positive patch contacts the major groove or the phosphate backbone of a DNA molecule and inhibits the binding or function of DNA-binding proteins. Many other groups suitable for the purposes of practicing this invention are well known and widely available to one skilled in the art The polyamide subunit structures I–VIII above may be covalently coupled through the γ residue which represents a —NH—CH$_2$—CH$_2$—CH$_2$—CONH— hairpin linkage derived from γ-aminobutyric acid or a chiral hairpin linkage derived from R-2,4-diaminobutyric acid. The present invention provides the reagents and methodologies for substituting the γ-residue of certain polyamides with a moiety such as (R)2,4,-diaminobutyric acid ((R)H$^{2,N}$γ). The NMR structure of a hairpin polyamide of sequence composition ImPyPy-γ-PyPyPy complexed with a 5'-TGTTA-3' target site indicated that it was possible to substitute the α-position of the γ-aminobutyric acid residue within the hairpin-DNA complex (de Claire, et al. *J. Am. Chem. Soc.* 1997, 119, 7909). Modeling indicated that replacing the α-H of γ with an amino group that may confer an R-configuration at the α-carbon could be accommodated within the floor and walls of the minor groove as demonstrated in FIGS. 1 and 2A. In contrast, the (S)-2,4,-diaminobutyric acid ((S)$^{H_2N}$γ) linked hairpin is predicted to clash with the walls of the minor groove of the DNA helix as illustrated in FIGS. 1 and 2B.

In Formulas V–VIII, L represents an amino acid linking group such as β-alanine or 5-aminovaleric acid (δ) bound to the γ residue of a first polyamide and to the carboxytail of a second polyamide. As such, two or more polyamides may be linked, forming a tandemly-linked polyamide. Such a polyamide is said to be tandemly-linked or a tandem-linked polyamide.

P represents from zero to ten polyamides of formulas IX–XII:

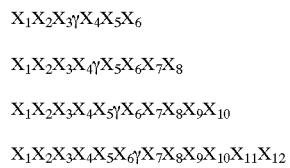

$$X_1X_2X_3\gamma X_4X_5X_6 \quad \text{IX}$$

$$X_1X_2X_3X_4\gamma X_5X_6X_7X_8 \quad \text{X}$$

$$X_1X_2X_3X_4X_5\gamma X_6X_7X_8X_9X_{10} \quad \text{XI}$$

$$X_1X_2X_3X_4X_5X_6\gamma X_7X_8X_9X_{10}X_{11}X_{12} \quad \text{XII}$$

that may be tandemly linked to another polyamide. Preferably, P represents from zero to eight polyamides of formulas IX–XII. More preferably, P represents from zero to six polyamides of formulas IX–XII. More preferably, P represents from zero to four polyamides of formulas IX–XII. Most preferably, P represents from zero to two polyamides of formulas IX–XII. In Formulas IX–XII, $X_1$–$X_{12}$ are as defined above. Tandem linking of polyamides provides expanded binding site size and increased binding affinity without compromising selectivity. Many other groups suitable for the purposes of practicing this invention are well known and widely available to one skilled in the art.

Baird, et al. (*J. Am. Chem. Soc.* 118: 6141–6146) and PCT/US97/003332 describe methods for synthesis of polyamides which are suitable for preparing polyamides of this invention. Polyamides of the present invention may be synthesized by solid phase methods using compounds such as Boc-protected 3-methoxypyrrole, imidazole, and pyrrole aromatic amino acids, which are cleaved from the support by aminolysis, deprotected with sodium thiophenoxide, and purified by reverse-phase HPLC. The identity and purity of the polyamides may be verified using any of a variety of analytical techniques available to one skilled in the art such as 1H-NMR, analytical HPLC, and/or matrix-assisted laser-desorption ionization time-of-flight mass spectrometry (MALDI-TOF MS-monoisotropic).

Described herein is the synthesis of a new class of polyamides and their characterization with regard to DNA binding affinity and sequence specificity. Revealed herein to one skilled in the art are properties of positive patch elements that may be utilized as a guide in the design of more efficient polyamides. The present invention provides one skilled in the art with the reagents and methodologies for the design, synthesis and utilization of polyamides comprising a positive patch. As a representative example, a series of polyamides with Arg-Pro-Arg tripeptides at the C-terminus are provided. It is demonstrated that such polyamides selectively inhibit DNA binding by the major groove-binding transcription factor GCN4, as measured by gel mobility shift assays. Polyamides having certain residues of the positive patch substituted are provided to identify the function of each amino acid in inhibition of protein binding. Also provided are DNase I footprint titration experiments to measure the effect of net ligand charge on both the DNA binding affinity and specificity of the hairpin polyamide. As demonstrated herein, addition of an Arg-Pro-Arg tripeptide does not result in significant alteration of polyamide-DNA binding affinity or specificity.

The instant invention provides polyamides that act as synthetic ligands to affect binding of proteins with affinity for the major groove of DNA, as well as methods of making and using such polyamides. In addition, sequences adjacent to or neighboring the protein binding site may be targeted, as exemplified by selective inhibition of GCN4 at two sites using Arg-Pro-Arg-polyamides. The Arg-Pro-Arg domain appears to adopt a stable and defined structure which delivers a neutralizing positive charge to the DNA backbone where it competes with GCN4 for contact to the phosphates. The broad targetable sequence repertoire of polyamides, coupled with the ubiquity of backbone contacts in protein recognition of DNA, make phosphate neutralization by a positive patch a promising approach for inhibition of major groove transcription factors.

One skilled in the art may utilize the examples provided herein to design polyamides comprising a positive patch sequence. The examples listed above and those illustrated below represent only certain embodiments of the present invention and are not limiting of the specification and claims in any way.

EXAMPLES

Example 1

Materials and Methods

All buffers for gel mobility shift and footprinting experiments were prepared from J.T. Baker reagents and 0.2 μM filtered. EDTA and DTT were obtained from Gibco BRL. Poly(dI-dC)·poly(dI-dC) was from Pharmacia Biotech. Ficoll (MW 400,000) was purchased from Sigma. T4 polynucleotide kinase, EcoRI, PvuII, and DNase I were from Boehringer Mannheim. AflII and FspI were purchased from New England Biolabs. Sequenase (version 2.0) was obtained from United States Biochemical. [α-$^{32}$P]-Thymidine-5'-triphosphate ($\geq$3000 Ci/mmol), [α-$^{32}$P]-deoxyadenosine-5'-triphosphate ($\geq$6000 Ci/mmol), and were purchased from Du Pont/NEN. [γ-$^{32}$P]-Adenosine-5'-triphosphate ($\geq$7000 Ci/mmol) was obtained from ICN. GCN4 (222–281) was prepared by solid phase synthesis. MBHA resin (0.57 mmol/g) was from Calbiochem. Boc-β-Ala, Boc-γ-aminobutyric acid, Boc-(Tos)Arg, Boc-Ala, Boc(CBz)Lys, Boc-Gly, Boc-Pro and Boc-D-Pro were from Peptides International. p-Cresol was purchased from Aldrich. All other chemicals, as well as the purification and characterization of polyamides were as previously described (Baird, et al. (1996) *J. Am. Chem. Soc.* 118, 6141–6146).

Example 2

Arg-Pro-Arg Polyamides

Schematic models of certain polyamides targeted to the binding site of the bZIP transcriptional activator GCN4 are illustrated in FIG. 1, parts a–d. A series of polyamides with Arg-Pro-Arg tripeptides at the C-terminus were synthesized by solid phase methods. The polyamides were evaluated as inhibitors of the major groove transcription factor GCN4, the prototypical member of the basic region-leucine zipper (bZIP) family of transcriptional regulators (Hurst, H. C. (1995) Protein Profile 2, 105–168; Struhl, K. (1992) Yeast GCN4 transcriptional activator protein. In Transcriptional Regulation. (McKnight, S. L. & Yamarmoto, K. R., eds), pp. 833–859, Cold Spring Harbor Laboratory Press, New York; Curran, T.& Vogt, P. (1992) Dangerous liasions: fos and jun, oncogenic transcription factors. In Transcriptional Regulation. (McKnight, S. L. & Yamamoto, K. R., eds), pp. 797–832, Cold Spring Harbor Laboratory Press, New York). The C-terminal sixty amino acids (222–281) of GCN4 contain the "leucine zipper" dimerization domain and the "basic region" which is responsible for DNA binding. GCN4 (222–281) has been shown to be sufficient for sequence specific binding (Oakley, et al. (1990) *Science* 248, 847–850; Hope, et al. (1986) *Cell* 46, 885–894; Paolella et al. (1994) *Science* 264, 1130–1133). The basic region of each α-helical monomer makes specific hydrogen bonds, van der Waals contacts, and phosphate interactions with one half-site of the nine base pair pseudosymmetrical GCN4 binding site (FIG. 2 A & B) (Oakley, et al. (1990), supra; Ellenberger, et al. (1992) *Cell* 71, 1223–1237; König, et al. (1993) *J. Mol. Biol.* 233, 139–154). The protein-DNA electrostatic interactions which are targeted for disruption by the Arg-Pro-Arg-polyamides are highlighted in FIG. 2B.

Figure 3:
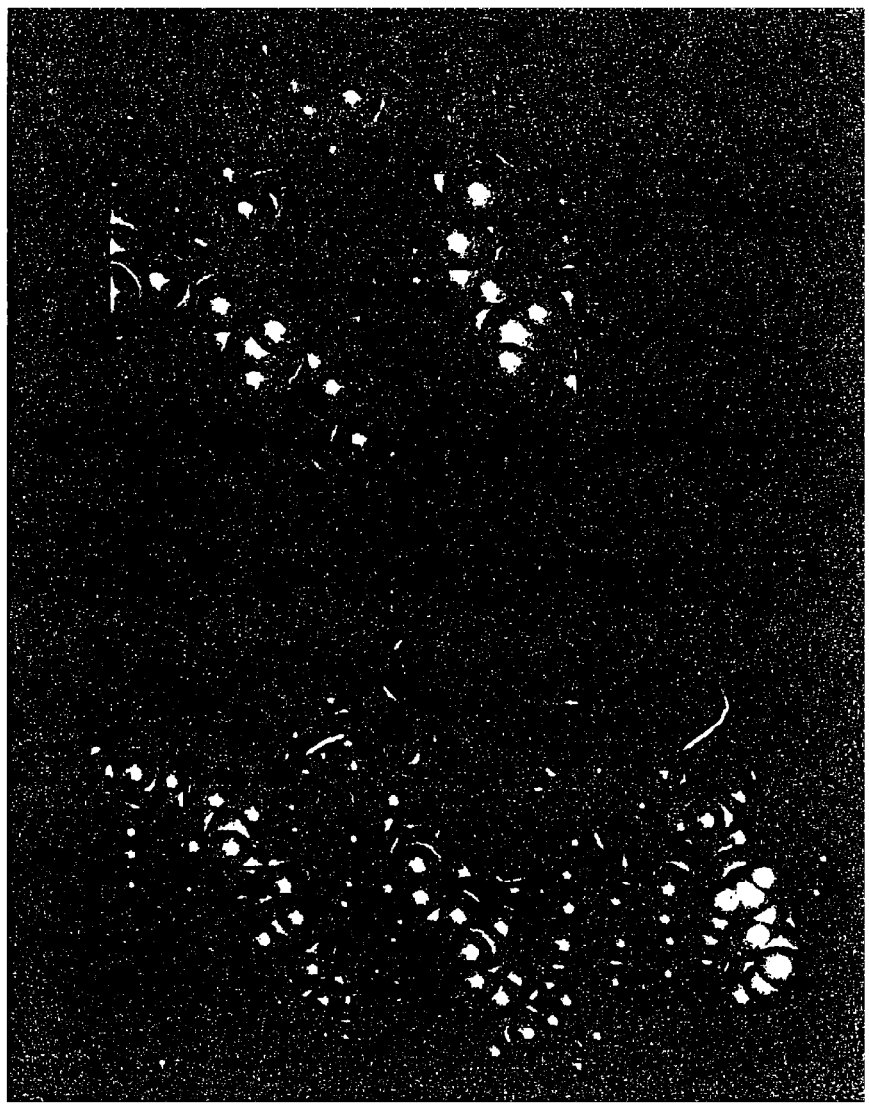
FIG. 3. Structure of DNA binding domain of Hin recombinase.

Homeodomain proteins recognize the minor groove of DNA via a highly conserved Arginine (Arg)-$X_{aa}$-Arg ($X_{aa}$= any amino acid) (Gehring, W. J., et al., & Wüthrich, K. (1994) Homeodomain-DNA recognition. *Cell* 78, 211–223; Gehring, et al. (1994) Homeodomain proteins. *Annu. Rev. Biochem.* 63, 487–526). In Hin recombinase, the corresponding Arg$^{140}$-Proline$^{141}$ (Pro)-Arg$^{142}$ domain serves as a bridge between the N-terminal arm in the minor groove and the helix-turn-helix motif which recognizes the major groove (Sluka, et al. (1990) *Biochemistry* 29, 6551–6561; Feng, et al. (1994) *Science* 263, 348–355). Minor groove contacts made by the side chain of Arg$^{140}$ direct the peptide chain up from the floor of the minor groove, toward the backbone, where the guanidinium of Arg$^{142}$ makes electrostatic contact with phosphates. Upon interaction with DNA, the Arg-Pro-Arg domain achieves a stable, local tertiary structure which is potentially based solely on the primary sequence. It was postulated that Arg-Pro-Arg attached at the C-terminus of a polyamide would adopt a similar structure to that of Arg$^{40}$-Pro$^{141}$-Arg$^{142}$ in Hin recombinase. The resulting Arg-Pro-Arg-polyamide could be used to place a neutralizing positive charge at a predetermined phosphate on the DNA backbone (FIG. 3). Arg-Pro-Arg-polyamide synthesis is exemplified here for polyamide 3.

ImPyPyPy-γ-PyPyPyPy-β-RPR (Compound 3)

Polyamides 1–4 are illustrated in FIGS. 4A–D. ImPyPyPy-γ-PyPyPyPy-β-RPR-MBHA-resin was synthesized in a stepwise fashion by machine-assisted solid phase methods [44] from MBHA resin (600 mg, 0.57 mmol/g, calculated as $L_{new}$(mmol/g)=$L_{old}/(1+L_{old}(W_{new}-W_{old})\times 10^{-3})$, where L is the loading (mmol of amine per gram of resin) and W is the weight (g mol$^{-1}$) of the growing peptide attached to the resin (Barlos, et al. (1991) *Int. J. Peptide Protein Res.* 37, 513–520). A sample of polyamide resin (300 mg, 0.30 mmol/g) was placed in a Kel-F reaction vessel, p-cresol (1 g) added, and the vessel cooled to –60° C. HF was then condensed into the vessel. The solution was stirred vigorously for one hour (0° C.) and the excess HF was removed in vacuo. The reaction mixture was then treated with cold ethyl ether (50 mL) and the resulting resin/polyamide coprecipitate was collected by vacuum filtration. The polyamide was then extracted with $CH_3CN:H_2O:TFA$ (10:9:1), 0.1% (w/v) TFA added (6 mL) and the resulting solution purified by reverse phase HPLC using a Waters DeltaPak 25×100 mm 100 μm $C_{18}$ column in 0.1% (w/v) TFA, gradient elution 0.25%/min. $CH_3CN$. ImPyPyPy-γ-PyPyPyPy-β-RPR-$NH_2$ was recovered upon lyophilization of the appropriate fractions as a white powder (84 mg, 60% recovery); UV ($H_2O$) $\lambda_{max}$ 244, 312 (66,000); $^1$H NMR (DMSO-$d_6$): δ 10.49 (s, 1H), 9.96 (s, 1H), 9.93 (s, 1H), 9.90 (s, 3H), 9.84 (s, 1H), 8.19 (d, 1H, J=7.6 Hz), 8.07 (m, 1H), 8.02 (m, 1H), 7.95 (m, 1H), 7.91 (m, 1H), 7.53 (m, 3H), 7.38 (s, 1H), 7.26 (d, 1H, J=1.6 Hz), 7.25 (s, 1H), 7.21 (d, 1H, J=1.6 Hz), 7.20 (s, 1H), 7.19 (s, 1H), 7.14 (m, 3H), 7.03 (m, 4H), 6.87 (d, 1H, J=1.6 Hz), 6.85 (m, 2H), 4.48 (t, 1H, J=4.8 Hz), 4.27 (q, 1H, J=4.4 Hz), 4.77 (m, 1H), 3.96 (s,3H) 3.81 (m, 12H), 3.80 (s, 3H), 3.77 (s, 3H), 3.76 (s, 3H), 3.60 (m, 2H), 3.32 (q, 2H, J=4.8 Hz), 3.17 (q, 2H, J=6.1 Hz), 3.0 (m, 4H), 2.36 (t, 2H, J=6.9 Hz), 2.25 (t, 2H, J=6.9 Hz), 2.0 (m, 2H), 1.77 (m, 4H), 1.64 (m, 2H), 1.46 (m, 6H).

Figure 4:
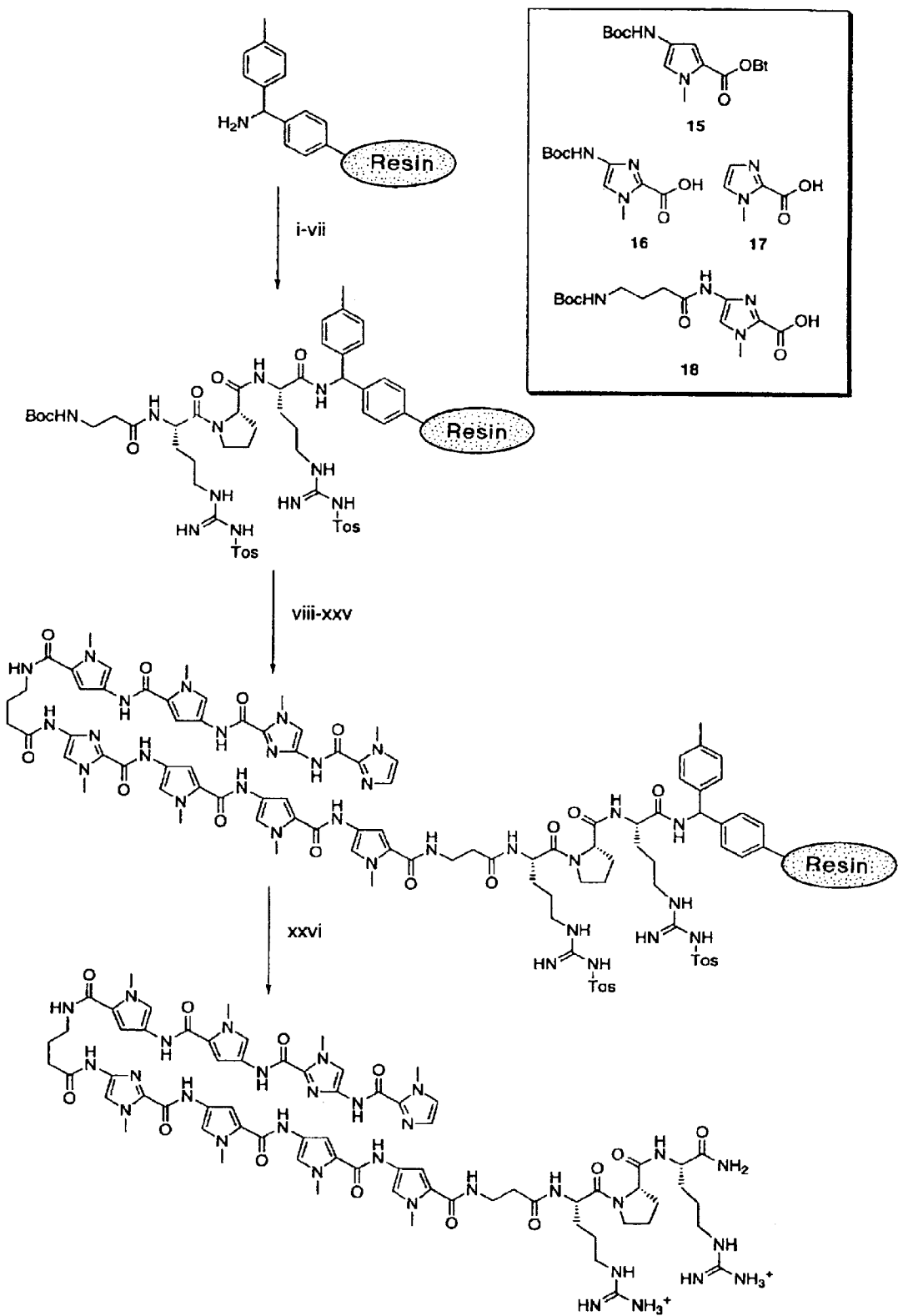
FIG. 4. Eight-ring hairpin polyamides.
Figure 5C:
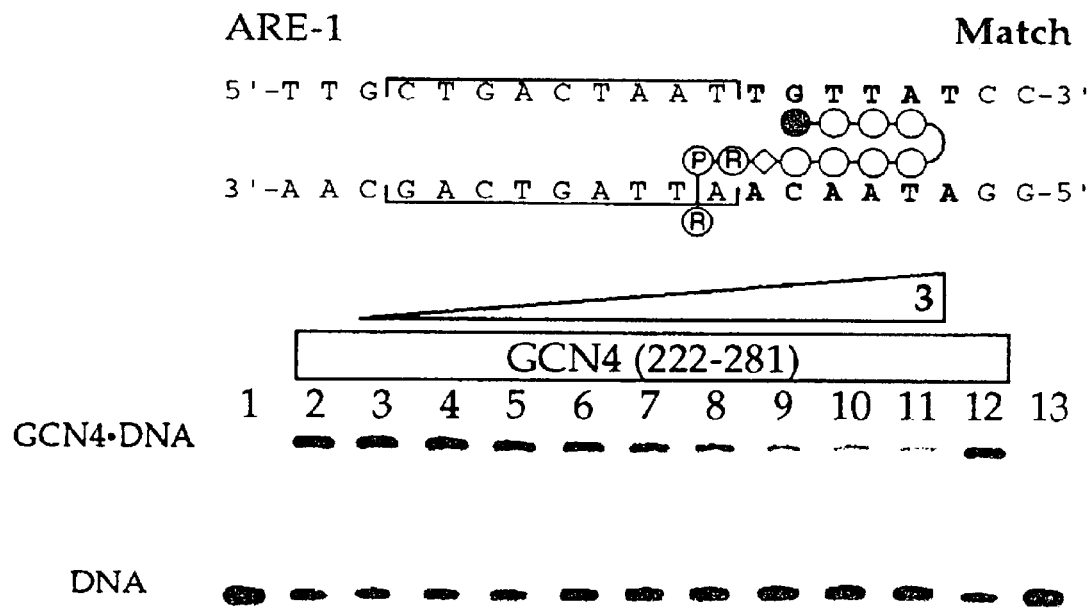
FIG. 5. Synthesis of Arg-Pro-Arg polyamides.
Figure 5D:
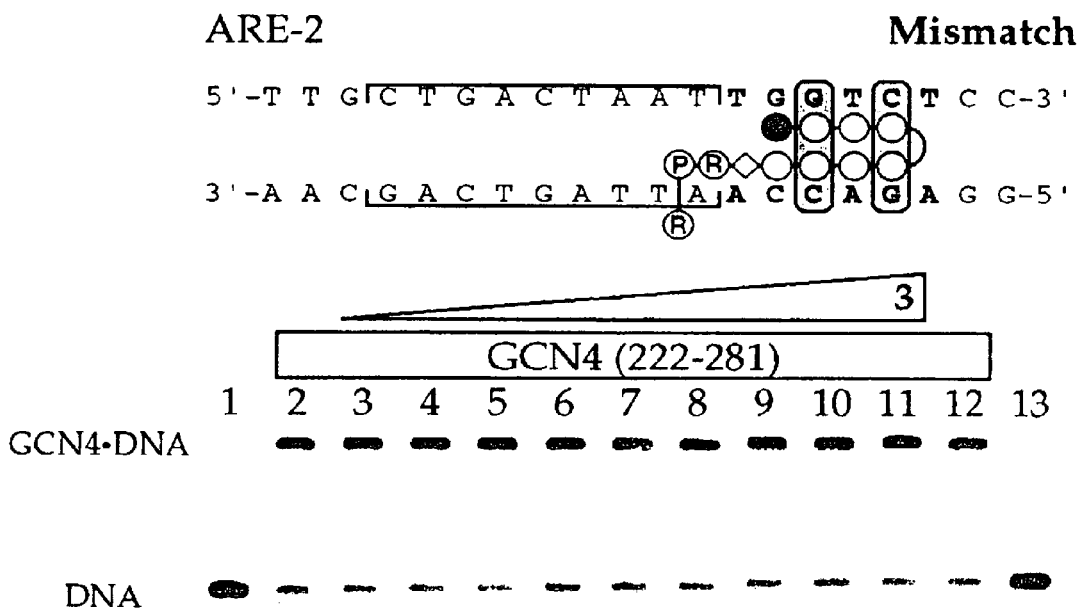
Figure 5E:
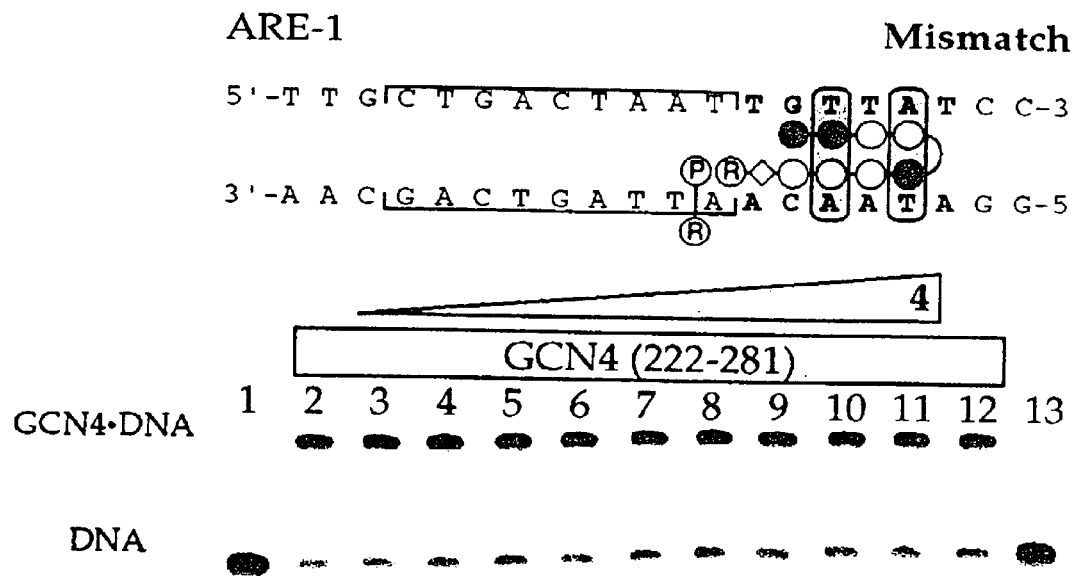
Figure 5F:
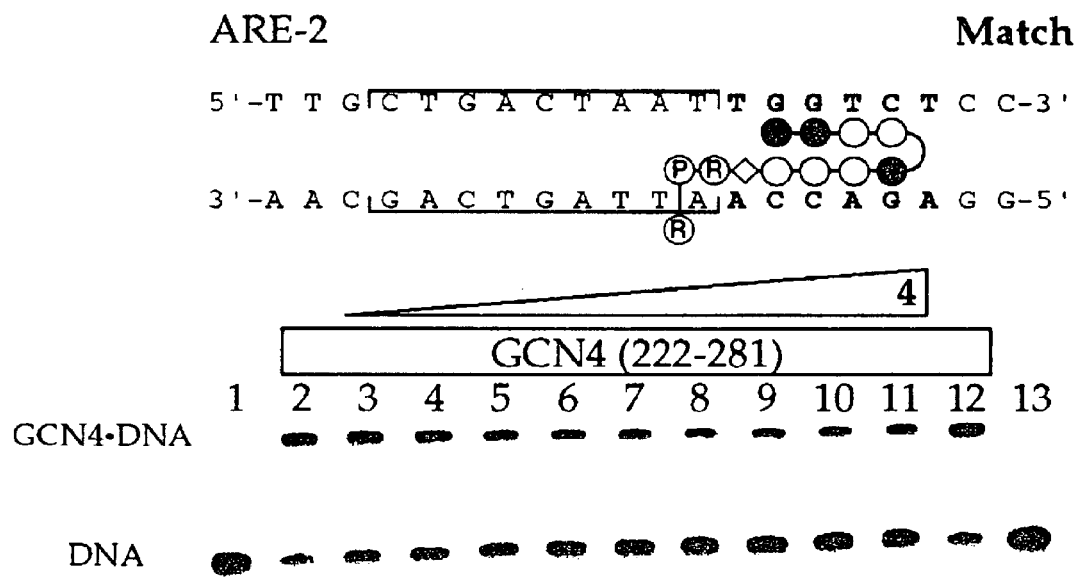
Figure 7A:
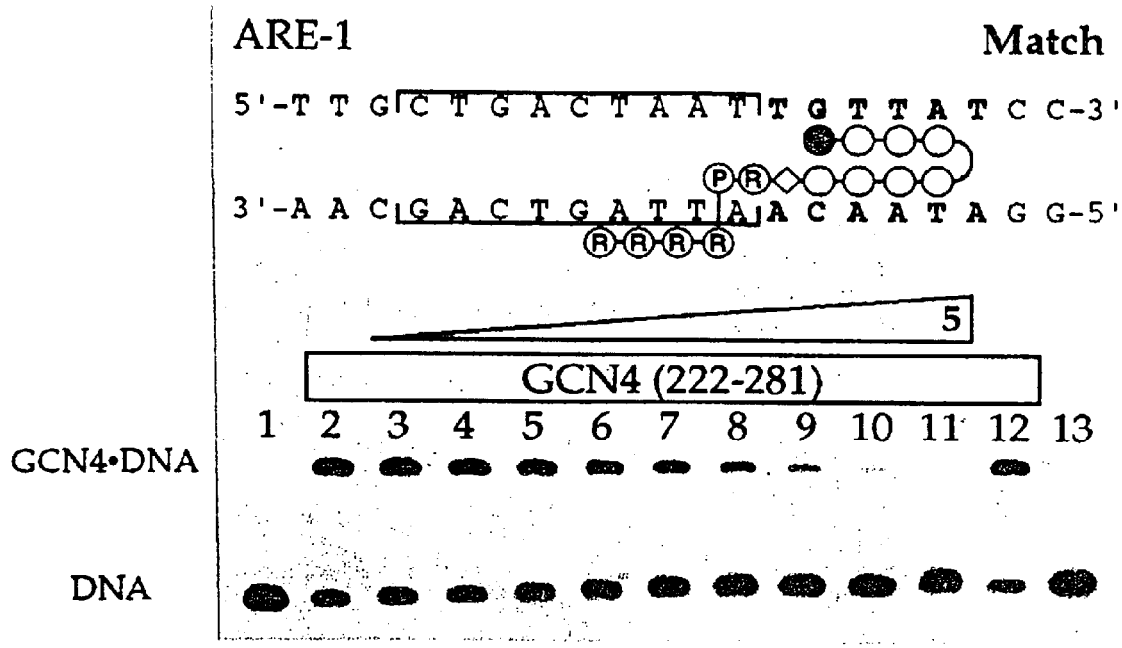
FIG. 7. Arg-Pro-Arg-Arg-Arg-Arg polyamides.
Figure 7B:
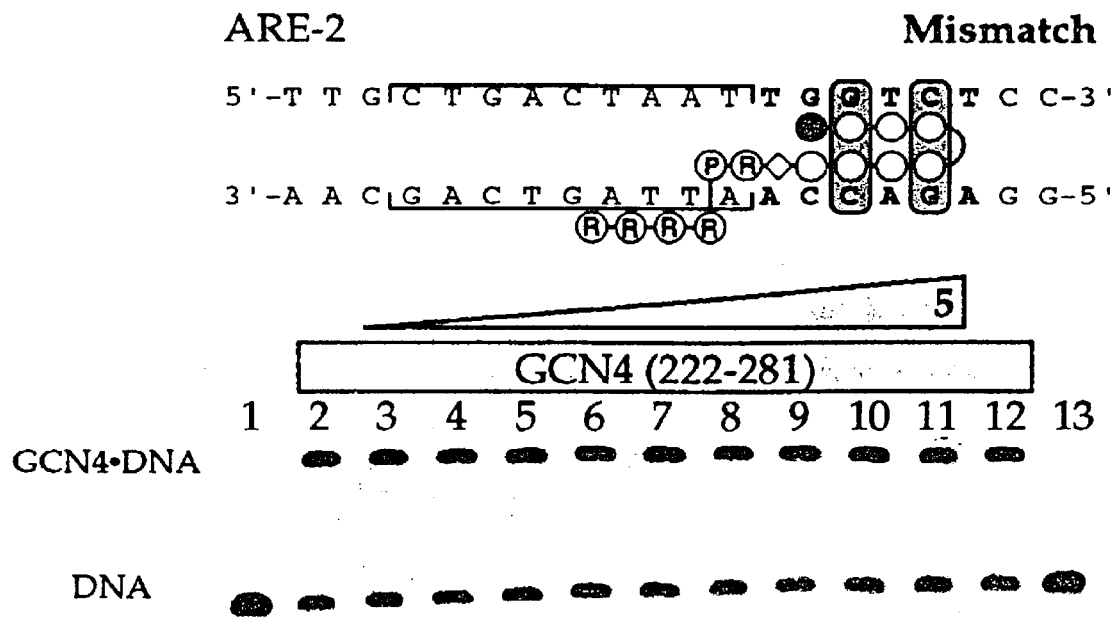
Figure 7C:
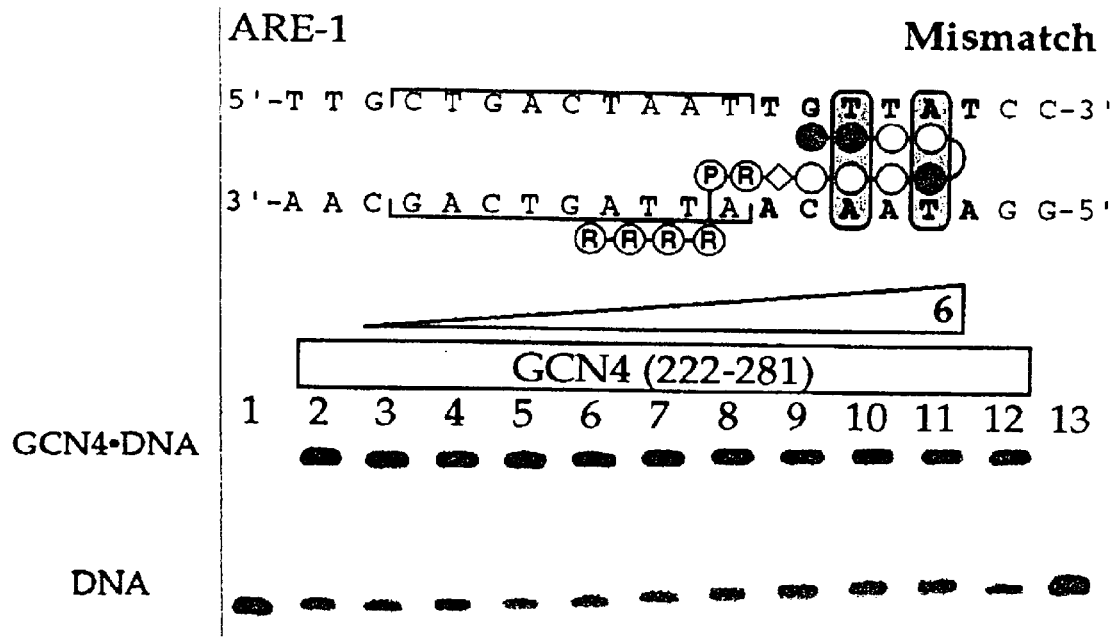
Figure 7D:
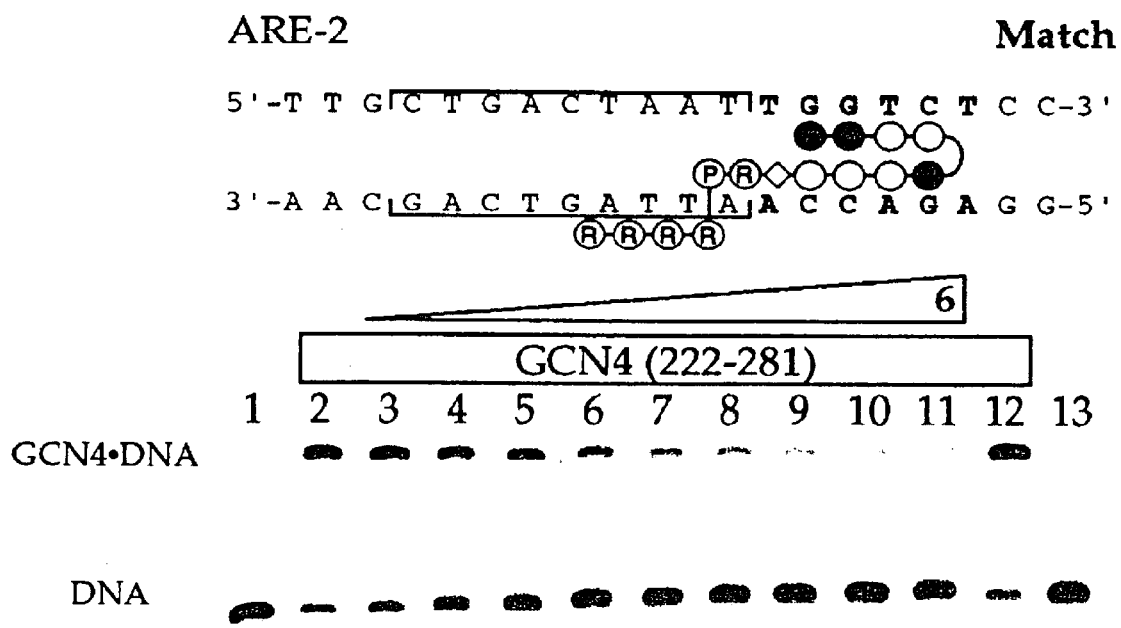

The polyamides ImPyPyPy-γ-PyPyPyPy-β-Dp (1) and ImImPyPy-γ-ImPyPyPy-β-Dp (2) were synthesized in a stepwise manner from Boc-β-alanine-Pam resin using Boc-chemistry machine-assisted protocols as previously described (Baird, et al. (1996) *J. Am. Chem. Soc.* 118, 6141–6146). Polyamides with C-terminal aliphatic amino acids were synthesized on MBHA resin from Im and Py monomer units and commercially available aliphatic amino acids in 26 steps (FIGS. 4 and 5). Treatment with HF:p-cresol (9:1) followed by precipitation with ethyl ether and extraction with 0.1% TFA:$CH_3CN$ (50:50) afforded the deprotected polyamide which was purified by reverse phase HPLC.

Example 3

Selective Inhibition of GCN4 (222–281) Binding by Arg-Pro-Arg Polyamides

Synthetic DNA fragments were prepared on an ABI 380B Automated DNA Synthesizer and purified by preparative denaturing polyacrylamide gel electrophoresis. ARE-1 (5'-CCGGATCCATGGTTGCTGACTAATTGTTATCCTCTA- GAGTCGACC-3') and ARE-2 (5'-CCGGATCCATGGTT-GCTGACTAATTGGTCTCCTCTAGAGTCG ACC-3') were radiolabeled at the 5'-terminus with γ-$^{32}$P-ATP and T4 polynucleotide kinase, annealed to an equimolar amount of the unlabeled complement, and purified by nondenaturing polyacrylamide gel electrophoresis (Sambrook, et al. *Molecular Cloning*. (2nd ed.). Cold Spring Harbor Laboratory Press: Cold Spring Harbor, N.Y.).

For gel mobility shifts, polyamide was incubated with radiolabeled synthetic DNA duplex (10 kcpm) in 40 µL reaction volumes of bisTris (10 mM, pH 7.0), NaCl (100 mM), DTT (1 mM), EDTA (1 mM), and poly(dI-dC)·poly(dI-dC) (50 µg/mL) for 16 hours at 22° C. (20 mM MOPS, pH 7.0, 140 mM KCl, 10 mM NaCl, 1 mM MgCl$_2$, 1 mM spermine was used to model ionic conditions in vivo). GCN4 (222–281) was added and equilibrated for 30 minutes. Loading buffer (15% Ficoll, 0.025% bromophenol blue) (10 µL) was added and 10 µL was immediately loaded onto a running 8% (29:1, acrylamide:bis-acrylamide) polyacrylamide gel (0.5×TBE, 280 V, 0.8 mm, 13 cm). Sufficient separation of the free DNA and the DNA·GCN4 (222–281) complexes was achieved within 45 minutes. Gels were dried and exposed to a storage phosphor screen (Molecular Dynamics) (Johnston, et al. (1990) *Electrophoresis* 11, 355).

Synthetic radiolabeled DNA duplexes, ARE-1 and ARE-2, containing a GCN4 binding site (5'-CTGACTAAT-3') (Oakley, et al. (1990) *Science* 248, 847–85029; Oakley, et al. (1992) *Biochemistry* 31, 10969–10975), were bound near saturation at 200 nM GCN4 (222–281) as revealed by gel mobility shift analysis (10 mM bisTris pH 7.0, 100 mM NaCl, 1 mM DTT, 1 mM EDTA, 50 µg/mL poly(dI-dC)·poly(dI-dC), 22° C.). ImPyPyPy-γ-PyPyPyPy-β-polyamides (1 and 3) target the six base pair 5'-TGTTAT-3' site adjacent to the GCN4 binding site of ARE-1 (FIG. 6). ImImPyPy-γ-ImPyPyPy-β-polyamides (2 and 4) were designed to bind 5'-TGGTCT-3' adjacent to the GCN4 site in ARE-2 (FIG. 6).

The ability of polyamides to inhibit GCN4 (222–281) binding was evaluated using the gel mobility shift assay. Increasing concentrations of polyamide were incubated with the desired radiolabeled synthetic DNA duplex followed by the addition of a constant concentration of 200 mM GCN4 (222–281). DNA fragments bound and unbound by GCN4 were separated using nondenaturing polyacrylamide gel electrophoresis.

Polyamides 1 and 2, which lack the Arg-Pro-Arg moiety were unable to inhibit GCN4 binding (FIG. 6). The upper band in FIG. 6A is the ARE-1 fragment bound by GCN4 (222–281) (lanes 2–12). Lanes 3–11 show that GCN4 binding was unaffected by the addition of ImPyPyPy-γ-PyPyPyPy-β-Dp. However, ImPyPyPy-γ-PyPyPyPy-β-RPR, which differs from 1 by the addition of the C-terminal Arg-Pro-Arg, inhibited GCN4 binding to ARE-1 (FIG. 6C). When bound to its match site on ARE-2, ImImPyPy-γ-ImPyPyPy-β-RPR also successfully inhibited GCN4 binding (FIG. 6F).

Based on the pairing rules for polyamide-DNA complexes, the sites 5'-TGTTAT-3' (ARE-1 fragment) and 5'-TGGTCT-3' (ARE-2 fragment) are for ImPyPyPy-γ-PyPyPyPy-RPR "match" and "double-base-pair mismatch" sites, respectively, and for ImImPyPy-γ-ImPyPyPy-RPR "double-base pair mismatch" and "match" sites, respectively. Incubation of GCN4 and up to 2 µM ImPyPyPy-γ-PyPyPyPy-β-RPR with the double mismatch ARE-2 fragment resulted in no inhibition of GCN4 binding (FIG. 6D). Likewise, ImImPyPy-γ-ImPyPyPy-β-RPR did not inhibit GCN4 binding to the mismatched ARE-1 fragment (FIG. 6E).

Figure 8A:
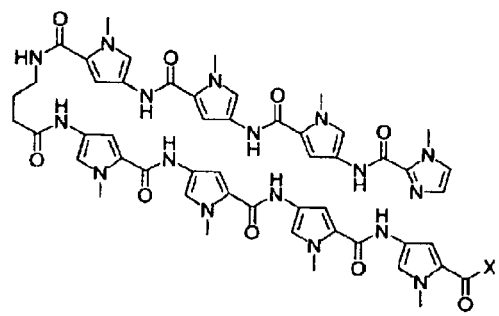
FIG. 8. GCN4 gel mobility shift experiments.
Figure 8B:
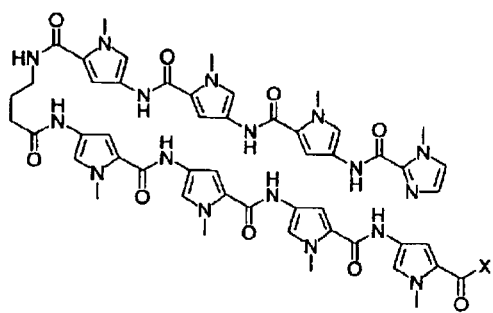

When bound to their respective match sites, ImPyPyPy-γ-PyPyPyPy-β-RPRRRR (5) and ImImPyPy-γ-ImPyPyPy-β-RPRRRR (6), which contain an additional three C-terminal arginine residues relative to 3 and 4, were found to fully inhibit GCN4 (222–281) binding (FIGS. 7 and 8). The gel mobility shift experiments depicted in FIG. 6 demonstrate that 5 and 6 selectively provided complete inhibition of GCN4 binding with no apparent loss in specificity for double-base-pair mismatches.

Example 4

Design of Optimum Tripeptide for GCN4 Inhibition

Figure 9:
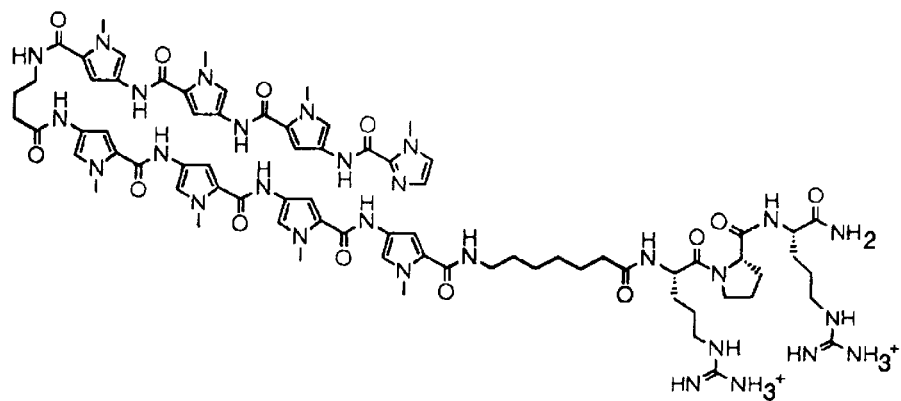
FIG. 9. Aliphatic amino acid substitutions in positive patch domain.
Figure 10A:
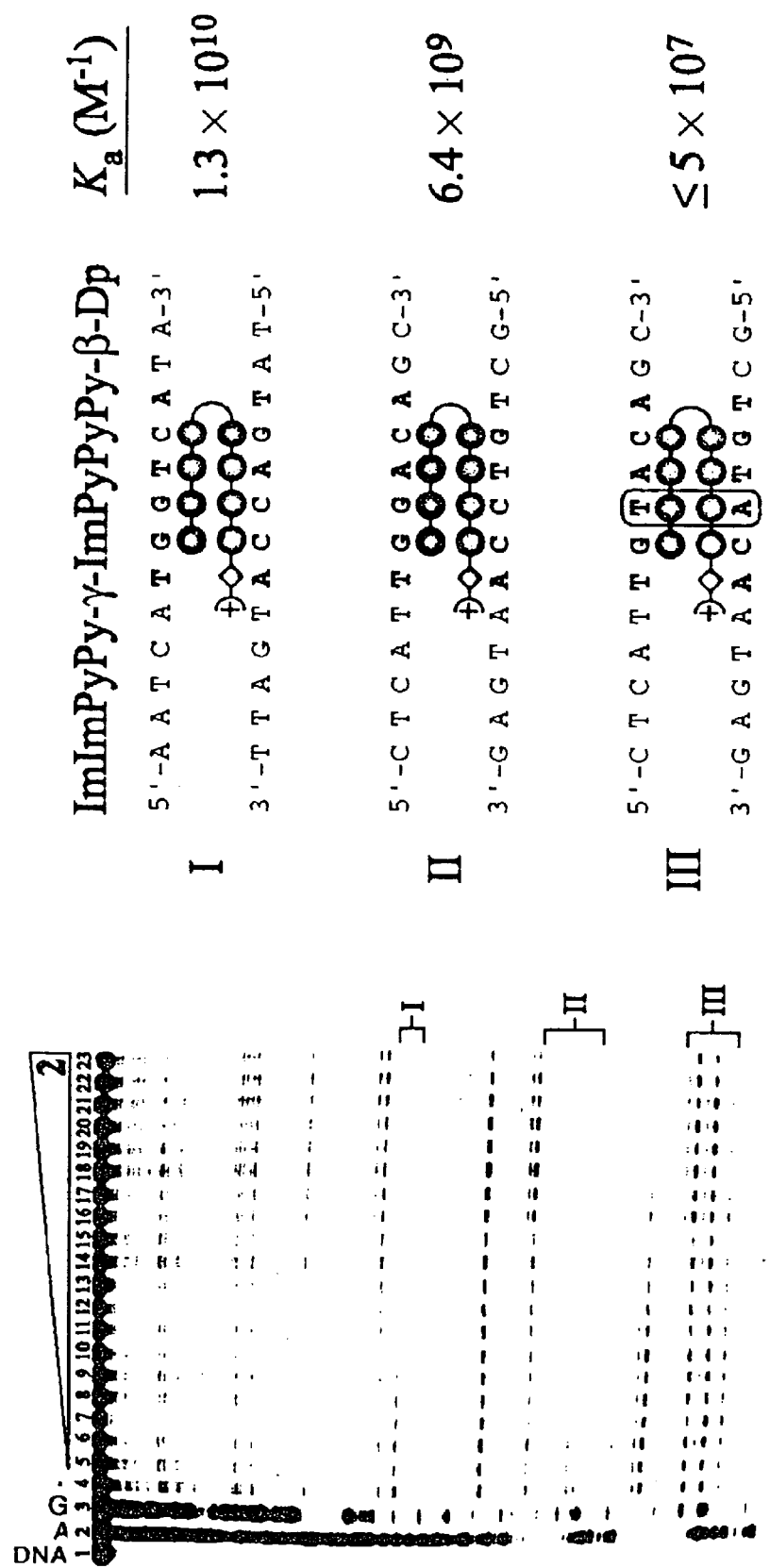
FIG. 10. Structure of ImPyPyPy-γ-PyPyPyPy-C7-RPR.
Figure 10B:
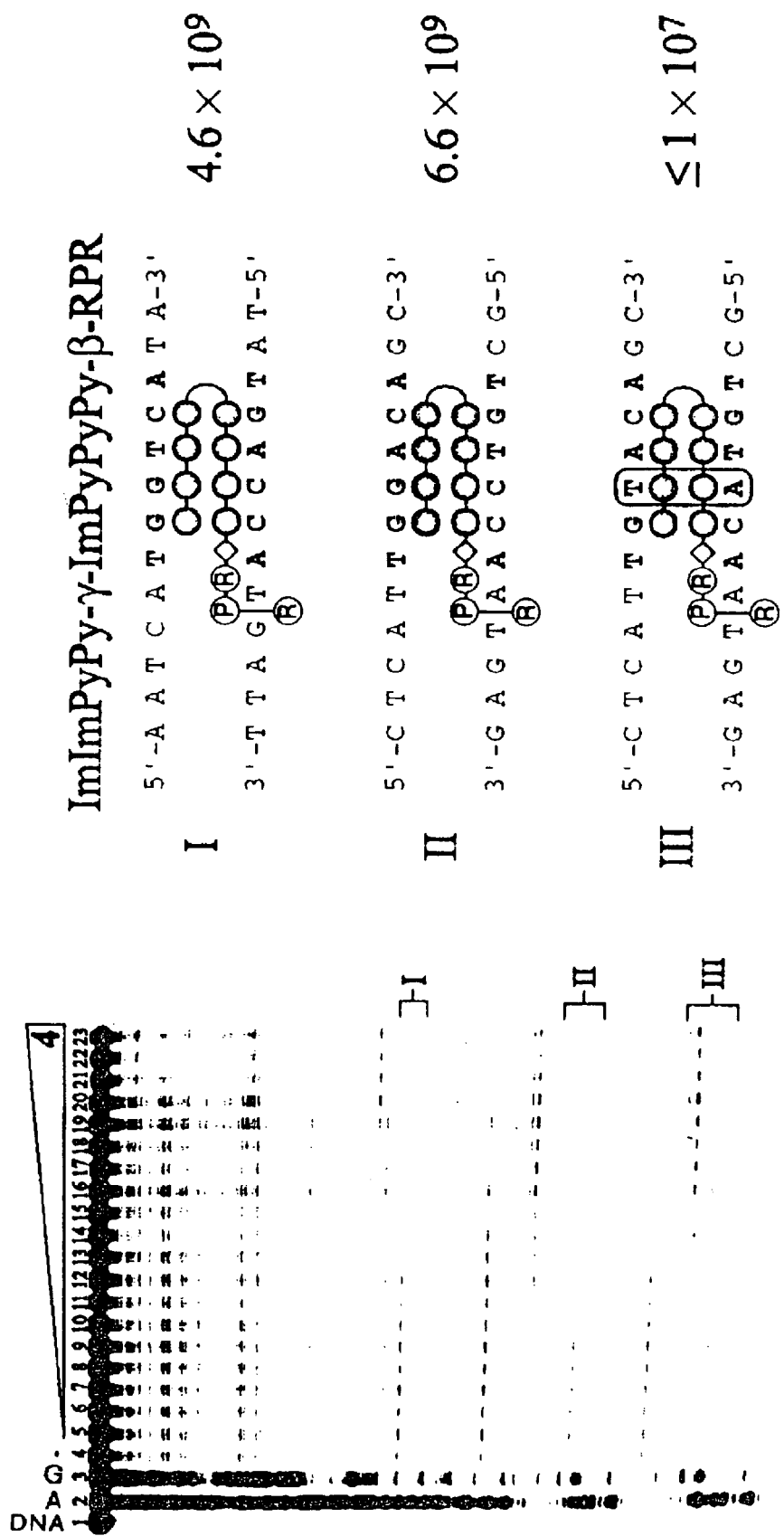

Polyamides with deletions and/or substitutions in the Arg-Pro-Arg domain were prepared in order to determine the elements which were essential for GCN4 inhibition (FIG. 9). Each of these polyamides was based on the ImPyPyPy-γ-PyPyPyPy-β polyamide targeted to 5'-TGTTAT-3' of ARE-1. The ability of polyamides 7–14 (FIGS. 9 and 10) to bind their DNA target sites and inhibit GCN4 binding to ARE-1 was evaluated using DNase I footprinting and gel mobility shift analysis.

Figure 11:
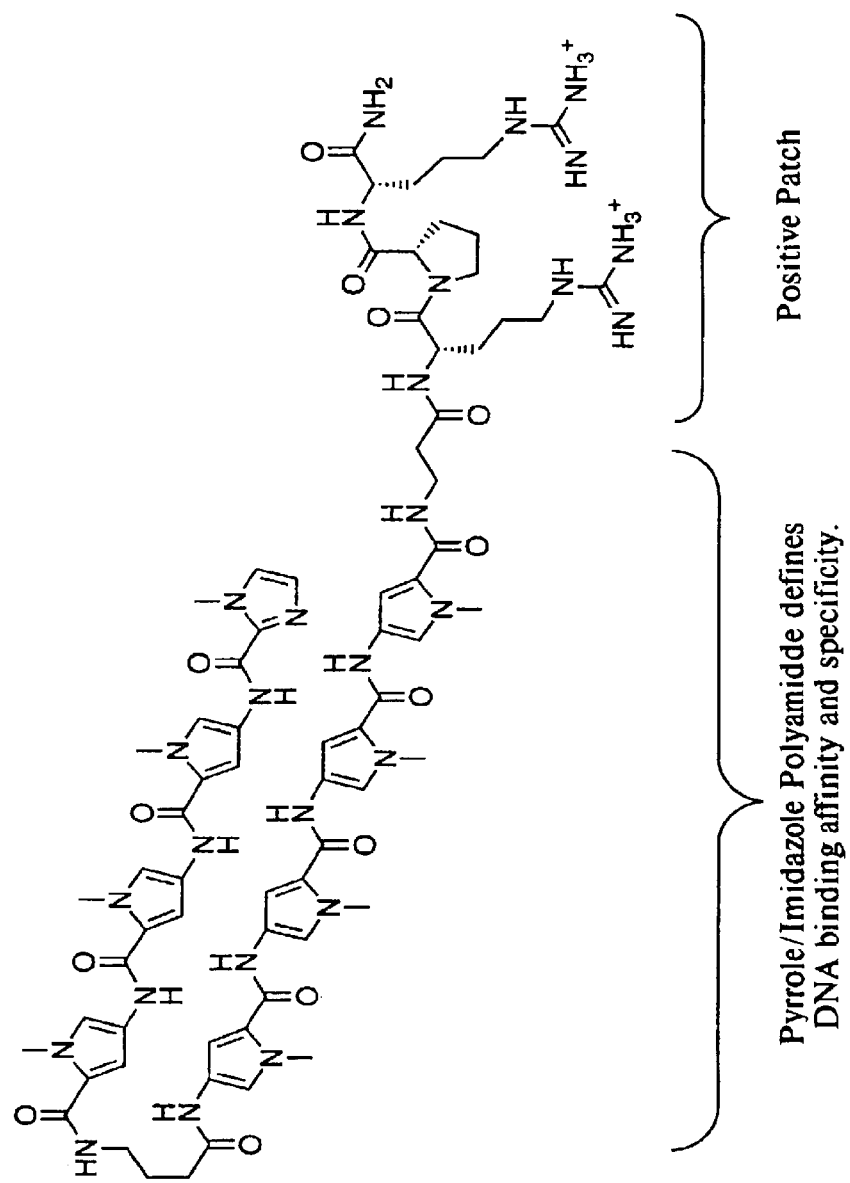
FIG. 11. Quantitative Dnase footprint experiments.

DNase I footprinting of polyamides 1–14 was performed on restriction fragments containing the appropriate ARE-1 or ARE-2 sequences under conditions identical to those used for the gel mobility shift experiments. In every case, (except 11, see below) the polyamide was found to specifically bind the target site with $K_a \sim 1 \times 10^7$ M$^{-1}$ (FIG. 11). Lower $K_a$ values are observed for polyamides under the gel shift conditions due to the carrier DNA which artificially depresses polyamide binding constants. The polyamide concentrations required for GCN4 inhibition are within the expected range based on the $K_a$ under gel shift conditions.

Deletion of the terminal Pro-Arg or Arg, as in ImPyPyPy-γ-PyPyPyPy-β-R, (7) and ImPyPyPy-γ-PyPyPyPy-β-RP (8), results in polyamides which are unable to inhibit GCN4 binding. Substituting the proline with glycine afforded ImPyPyPy-γ-PyPyPyPy-β-RGR (9), which did not effectively inhibit GCN4 (222–281). At 1 µM of 9, <50% of the GCN4 was inhibited. No inhibition of GCN4 binding was observed for ImPyPyPy-γ-PyPyPyPy-β-R$^D$PR (10) which contained a single inversion of stereochemistry relative to 3.

The internal arginine was replaced with an alanine residue to provide ImPyPyPy-γ-PyPyPyPy-β-APR (11). 11 was unable to inhibit GCN4 binding under these conditions. This Arg to Ala substitution was the only alteration which was found to affect polyamide binding affinity. By DNase I footprinting, 11 binds the 5'-TGTTAT-3' target site with ten-fold lower affinity than 3 under conditions identical to those used for gel shift analysis. The conservative substitution of lysine for arginine in ImPyPyPy-γ-PyPyPyPy-β-KPR (12) also compromised the polyamide's ability to inhibit GCN4; At 1 µM 12, <50% of the bound GCN4 was inhibited, similar to 9. However, the identical substitution in the C-terminal position afforded ImPyPyPy-γ-PyPyPyPy-β-RPK (13), which inhibited GCN4 binding identically to the Arg-Pro-Arg polyamide 3. The amino acid linkage between the final Py amino acid and the initial arginine was also crucial for GCN4 inhibition. A polyamide in which the β-alanine linker was replaced with a 7-aminoheptanoic acid linker, ImPyPyPy-γ-PyPyPyPy-C7-RPR (14), was unable to inhibit GCN4 binding. Protein inhibition did not require prebinding of polyamide. Preincubation of ARE-1 with GCN4 followed by addition of 5 afforded inhibition identical to that of prebound polyamide.

By targeting an 8-ring Arg-Pro-Arg-polyamide adjacent to a GCN4 binding site, selective inhibition of DNA binding by a protein which exclusively contacts the major groove is achieved (FIGS. 4 and 6). The polyamide domain binds sequence specifically in the minor groove with double base pair mismatches preventing GCN4 inhibition.

The inability of truncated analogs 7 (R) or 8 (RP) to inhibit GCN4 binding indicates that the C-terminal arginine in 3 (RPR) is crucial for GCN4 inhibition. Based on the Hin recombinase model, this arginine is expected to make non-specific contacts to the DNA phosphate backbone. The ability of 13 (RPK) to inhibit GCN4 identically to 3 (RPR) supports this model. The neutralization of a portion of the backbone is the most likely mechanism by which Arg-Pro-Arg polyamides achieve GCN4 inhibition. Other models, such as steric blockage of the major groove or DNA distortion, cannot be ruled out (Strauss, et al. (1994) *Science* 266, 1829–1834). Modeling suggests that Arg-Pro-Arg is insufficient to cross the DNA backbone and block the major groove. Determination of the exact mechanism of inhibition awaits high-resolution structure studies which are in progress.

The results of GCN4 inhibition experiments with polyamides 7–14 suggest that the Arg-Pro-Arg of 3 and 4 adopts a stable and well-defined structure similar to $Arg^{140}$-$Pro^{141}$-$Arg^{142}$ of Hin recombinase. The internal Arg-Pro of 3 and 4 (RPR) is required for GCN4 inhibition. Polyamide 8 does not inhibit GCN4, suggesting that these two residues play a structural role in the placement of the terminal arginine near the phosphate backbone. Replacing the rigid proline of 3 (RPR) with a flexible glycine (9) (RGR) allows significant amounts of GCN4 to remain bound in the presence of saturating concentrations of 9. The glycine in 9 may permit the C-terminal arginine to shift to a position which permits simultaneous binding with GCN4.

ImPyPyPy-γ-PyPyPyPy-β-$R^D$PR (10) is a diastereomer of ImPyPyPy-γ-PyPyPyPy-β-RPR (3), but is unable to inhibit GCN4. Modeling indicates that substitution of D-proline for L-proline may in fact direct the neutralizing terminal arginine to the backbone of the opposite DNA strand. However, confirmation of this prediction awaits studies with other protein systems.

Replacement of the internal arginine with alanine, as in 11, reduces binding affinity by a factor of ten and prevents GCN4 inhibition. Furthermore, the Lys-Pro-Arg polyamide, 12, exhibits a binding affinity comparable to 3, yet it is a less effective inhibitor of GCN4. Together, these results suggest that the guanidinium of the internal arginine makes specific contacts with the DNA which are required for the proper positioning of the remaining residues. Replacement of the β-alanine linker (3) with 7-aminoheptanoic acid (14) eliminates inhibition, further implicating the placement of the Arg-Pro-Arg moiety as a requirement for effective inhibition.

Example 5

Salt Dependence of Positive Patch Polyamides

In order to evaluate the sensitivity of positive patch mediated major groove protein inhibition to the nature of the compensating electrolyte, as well as the overall ionic strength, gel mobility shift analysis was performed using a buffer which models the environment of the cellular nucleus (20 mM MOPS, pH 7.2, 140 mM KCl, 10 mM NaCl, 1 mM $MgCl_2$, 1 mM spermine) (Jones, et al. (1993) *J. Org. Chem.* 58, 2983–2991). Arg-Pro-Arg-polyamide 3 was found to inhibit GCN4 (222–281) binding under the in vivo ionic conditions which feature KCl as the primary compensating electrolyte and the conditions optimized for protein binding which feature NaCl as the predominant compensating electrolyte (FIG. 6C). Further biophysical characterization of major groove protein inhibition by positive patch polyamides will be reported in due course.

Example 6

Arg-Pro-Arg Polyamide Binding Affinity and Specificity

In order to evaluate the effects of the Arg-Pro-Arg moiety on the DNA binding properties of the polyamides, quantitative DNase I footprint titration experiments were performed to determine the equilibrium association constants of polyamides 1–6 for their respective six base pair match and single-base-pair mismatch sites (10 mM Tris pH 7.0, 10 mM KCl, 10 mM $MgCl_2$, 5 mM $CaCl_2$, 22° C.) (Brenowitz, et al. (1986) *Methods Enzymol.* 130, 132–181).

The AflII/FspI restriction fragment of pJT8 (Trauger, et al. (1996) *Nature* 382, 559–561) was 3'-$^{32}$P-end-labeled by digesting the plasmid with AflII and FspI and simultaneously filling in using Sequenase, [α-$^{32}$P]-deoxyadenosine-5'-triphosphate, and [α-$^{32}$P]-thymidine-5'-triphosphate, and isolating the 229 bp fragment by nondenaturing gel electrophoresis. The 250 bp EcoRI/PvuII restriction fragment of pJK6 (Struhl, K. (1992) Yeast GCN4 transcriptional activator protein. In *Transcriptional Regulation*. (McKnight, S. L. & Yamamoto, K. R., eds), pp. 833–859, Cold Spring Harbor Laboratory Press, New York) was prepared in an analogous manner. A and G sequencing were carried out as described (Maxam, et al. (1980) *Methods Enzymol.* 65, 499–560; Iverson, et al. (1987). *Methods Enzymol.* 15, 7823–7830).

All reactions were executed in a total volume of 400 μL. A polyamide stock solution or $H_2O$ (for reference lanes) was added to an assay buffer containing radiolabeled restriction fragment (20 kcpm), affording final solution conditions of 10 mM Tris.HCl (pH 7.0), 10 mM KCl, 10 mM $MgCl_2$, 5 mM $CaCl_2$, and either (i) 0.001 nM–100 nM polyamide or (ii) no polyamide (for reference lanes). The solutions were allowed to equilibrate at 22° C. for 18 h. Footprinting reactions were initiated by the addition of 4 μL of a DNase I stock solution (at the appropriate concentration to give ~55% intact DNA) containing 1 mM dithiothreitol and allowed to proceed for seven min at 22° C. The reactions were stopped by the addition of 50 μL of a solution containing 1.25 M NaCl, 100 mM EDTA, 0.2 mg/mL glycogen, and 28 μM base-pair calf thymus DNA, and ethanol precipitated. Reactions were resuspended in 1×TBE/80% formamide loading buffer, denatured by heating at 85° C. for 10 min, and placed on ice. The reaction products were separated by electrophoresis on an 8% polyacrylamide gel (5% cross-link, 7 M urea) in 1×TBE at 2000 V for 1.5 h. Gels were dried and exposed to a storage phosphor screen (Molecular Dynamics) (Johnston, et al. (1990) *Electrophoresis* 11, 355).

Data from the footprint titration gels were obtained using a Molecular Dynamics 400S PhosphorImager followed by quantitation using ImageQuant software (Molecular Dynamics). Background-corrected volume integration of rectangles encompassing the footprint sites and a reference site at which DNase I reactivity was invariant across the titration generated values for the site intensities ($I_{site}$) and the reference intensity ($I_{ref}$). The apparent fractional occupancy ($\theta_{app}$) of the sites were calculated using the equation:

$$\theta_{app} = 1 - \frac{I_{site}/I_{ref}}{I^o_{site}/I^o_{ref}} \quad (1)$$

where $I^o_{site}$ and $I^o_{ref}$ are the site and reference intensities, respectively, from a control lane to which no polyamide was added. The ($[L]_{tot}, \theta_{app}$) data points were fit to a Langmuir binding isotherm (eq 2, n=1) by minimizing the difference between $\theta_{app}$ and $\theta_{fit}$, using the modified Hill equation:

$$\theta_{fit} = \theta_{min} + (\theta_{max} - \theta_{min})\frac{K_a^n[L]_{tot}^n}{1 + K_a^n[L]_{tot}^n} \quad (2)$$

where $[L]_{tot}$ is the total polyamide concentration, $K_a$ is the equilibrium association constant, and $\theta_{min}$ and $\theta_{max}$ are the experimentally determined site saturation values when the site is unoccupied or saturated, respectively. The data were fit using a nonlinear least-squares fitting procedure with $K_a$, $\theta_{max}$, and $\theta_{min}$ as the adjustable parameters. All acceptable fits had a correlation coefficient of R>0.97. At least three sets of data were used in determining each association constant. All lanes from each gel were used unless visual inspection revealed a data point to be obviously flawed relative to neighboring points.

DNase I footprinting of ImImPyPy-γ-ImPyPyPy-β-Dp (2), ImImPyPy-γ-ImPyPyPy-β-RPR (4), and ImImPyPy-γ-ImPyPyPy-β-RPRRRR (6) was performed on the 250 bp EcoRI/PvuII restriction fragment of pJK6 (Kelly, et al. (1993) *Proc. Natl. Acad. Sci., USA* 93, 6981–6985). 2 bound the match sites, 5'-TGGTCA-3' and 5'-TGGACA-3', with identical affinities within experimental error ($K_a$=1.3 (±0.1)×10$^{10}$ M$^{-1}$ and 6.4 (±1.2)×10$^9$ M$^{-1}$, respectively). 2 also demonstrated greater than 100-fold specificity for a single base pair mismatch site 5'-TGTACA-3' ($K_a \leq 5 \times 10^7$ M$^{-1}$, mismatched base pair underlined). Similar affinity and a slight increase in specificity were observed for Arg-Pro-Arg polyamide 3. 5'-TGGTCA-3' and 5'-TGGACA-3' were bound by 3 ($K_a$=4.6 (±0.2)×10$^{10}$ M$^{-1}$ and 6.6 (±1.0)×10$^{10}$ M$^{-1}$, respectively) with greater than 450-fold specificity versus the mismatch site ($K_a = \leq 1 \times 10^7$ M$^{-1}$). The additional three terminal arginines of 6 generated a ten-fold increase in affinity relative to 2 coupled with a significant loss in specificity for a single-base-pair mismatch. 6 bound 5'-TGGTCA-3', 5'-TGGACA-3', and 5'-TGTACA-3' with affinities of 2.6 (±0.4)×10$^{10}$ M$^{-1}$, 2.8 (±0.5)×10$^{10}$ M$^{-1}$ and 1.9 (±0.8)×10$^{10}$ M$^{-1}$, respectively.

Corresponding results were observed for DNase I footprinting of ImPyPyPy-γ-PyPyPyPy-β-Dp (1), ImPyPyPy-γ-PyPyPyPy-β-RPR (3) and ImPyPyPy-γ-PyPyPyPy-β-RPRRRR (5) on the 229 bp AflII/FspI restriction fragment of pJT8 (Trauger, et al. (1996) *Nature* 382, 559–561). 1 has been shown to bind its six base pair match site, 5'-AGTTAT-3', with an affinity of 3.5 (±0.8)×10$^9$ M$^{-1}$ and 7-fold specificity versus a single base pair mismatch site 5'-AGTACT-3' ($K_a$=5.0 (±0.5)×10$^8$ M$^{-1}$, Table 3) (Trauger, et al. (1996) *Nature* 382, 559–561).

TABLE 3

Equilibrium Association Constants (M$^{-1}$)

| Polyamide | 5'-AGTATT-3' | 5'-AGTACT-3' |
|---|---|---|
| ImPyPyPy-γ-PyPyPyPy-β-Dp | 3.5 × 10$^9$* | 5.0 × 10$^8$* |
| ImPyPyPy-γ-PyPyPyPy-β-RPR | 5.5 × 10$^8$ | 9.2 × 10$^7$ |
| ImPyPyPy-γ-PyPyPyPy-β-RPRRRR | 1.0 × 10$^{10}$ | 3.4 × 10$^9$ |

TABLE 3-continued

Equilibrium Association Constants (M$^{-1}$)

| Polyamide | 5'-AGTATT-3' | 5'-AGTACT-3' |
|---|---|---|

*Values reported for the six-base pair match (5'-AGTATT-3') and mismatch (5'-AGTACT-3') (mismatch underlined) sites are the mean values obtained from three Dnase I footprint titration experiments on the AflII/Fsp I restriction fragment of pJT8. The assays were carried out at 22° C. at pH 7.0 in the presence of 10 mM Tris · HCl, 10 mM KCl, 10 mM MgCl$_2$, and 5 mM CaCl$_2$.
*From Trauger, et al. (1996) Nature 382, 559–561.

The Arg-Pro-Arg polyamide 3 demonstrated only a slight loss in affinity and a similar specificity ($K_a$=5.5 (±1.5)×10$^8$ M$^{-1}$ for 5'-AGTATT-3' and 9.2 (±0.4)×10$^7$ M$^{-1}$ for 5'-AGTACT-3'). Analogous to 6, the additional terminal arginines of 5 provided a ten-fold increase in affinity for the match site ($K_a$=1.0 (±0.2)×10$^{10}$ M$^{-1}$) and a severe loss in specificity for a single-base-pair mismatch ($K_a$=3.4(±0.5)×10$^9$ M$^{-1}$).

Quantitative DNase I footprinting demonstrates that the addition of a C-terminal Arg-Pro-Arg tripeptide as in 3 and 4 does not alter the DNA binding properties of eight-ring hairpin polyamides (1 and 2). However, Arg-Pro-Arg-Arg-Arg-Arg-polyamides, 5 and 6, have increased binding affinity but no specificity for a single base pair mismatch site. DNase I footprinting and gel mobility shift analysis demonstrate that 5 and 6 retain their specificity versus double base pair mismatch sites. These results indicate that synthetic ligands may balance the benefits of additional charge with the consequence of lowered sequence specificity (Breslauer, et al. (1988) The origins of the DNA binding affinity and specificity of minor groove directed ligands: correlations of thermodynamic and structural data. In *Structure and Expression* (Vol. 2), *DNA and Its Drug Complexes* (Sarma, R. H. & Sarma, M. H. eds), pp. 273–289, Academic Press). For example, a distamycin analog modified with a decaaza decabutylamine moiety on a pyrrole nitrogen interferes with binding of a major groove transcription factor (Bruice, et al. (1997) *Bioorg. Med. Chem.* 5, 685–692). Unfortunately, the sequence specificity of this molecule which contains potentially eleven positive charges has not been reported. The results described here suggest that such a molecule may bind DNA with reduced sequence specificity.

Example 7

Inhibition of DNA-Binding Proteins by Polyamides

Oligonucleotides were synthesized and purified as previously described (Liberles, et al. (1996) Proc. Natl. Acad. Sci., USA 93, 9510–4). Polyamides were also synthesized as previously described and by Baird, et al. (1996, J. Am. Chem. Soc. 118, 6141–6). Briefly, synthesis was performed in a stepwise manner from Boc-β-Alanine-Pam resin. Polyamides were then cleaved by reaction with ((dimethylamino) propyl)-amine and purified by HPLC chromatography.

To prepare labeled DNA, plasmid DNA was digested with HindIII and EcoRI for gel shift analysis, or PvuII and EcoRI for footprinting analysis, and simultaneously labeled with Sequenase 2.0, deoxyadenosine 5'-(α-$^{32}$P)-triphosphate, thymidine 5'-(α-$^{32}$P)-triphosphate, and nonradioactive deoxynucleoside triphosphates. The fragment was purified by gel electrophoresis, treated with proteinase K, filtered, further extracted with phenol/chloroform, and precipitated with ethanol.

For DNase I and MPE footprint reactions, all reactions were equlibrated at 22° C., pH 5.5, in the presence of 45 mM MES, 1 mM MgCl$_2$, and labeled DNA for at least 24 hours. Footprinting reactions were carried out as previously described (Hertzberg, et al. (1984) Biochemistry. 23, 3934–3945; Brenowitz, et al. (1986) Proc. Natl. Acad. Sci., USA 83, 8462–8466.).

To perform gel shift assays and titrations, all samples were equilibrated as above for at least 24 hours. One-tenth volume of 15% glycerol loading buffer was added and samples were run on a 10% polyacrylamide gel at 40° C., pH 5.5, with a 75:1 acrylamide/bis-acrylamide ratio in 45 mM Mes and 1 mM MgCl$_2$ with buffer recirculation. Quantitation of isotherms was performed by plotting the ligand concentration against the portion of labeled DNA in the bent conformation and curve fit using a Langmuir binding isotherm, as previously described (Brenowitz, et al. (1986) Proc. Natl. Acad. Sci., USA 83, 8462–8466; Bailly, et al. (1995) J. Molecular Biology 253, 1–7).

Figure 13:
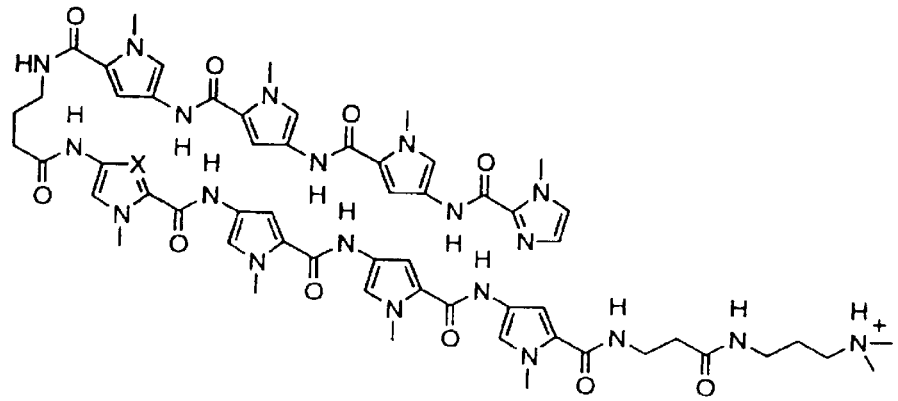
FIG. 13. Binding domains and chemical structures of PA1 and PA2.
Figure 14:
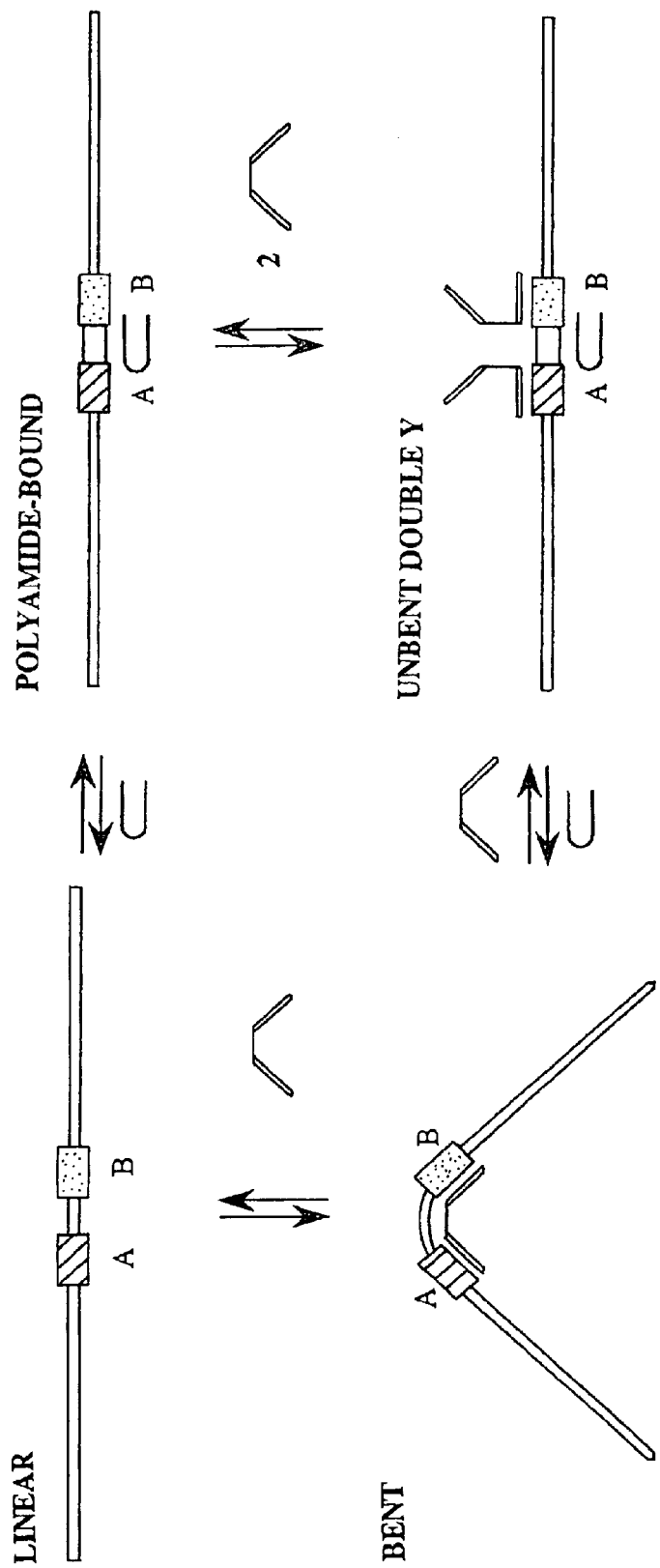
FIG. 14. Gel shift analysis of oligonucleotides 2–6, 9 on a $3'^{32}P$ end-labeled restriction fragment.
Figure 15:
FIG. 15. Gel shift analysis of oligonucleotides 2 (A) and 9 (B) on a $3'^{32}P$ end-labeled restriction fragment.

Two 15 bp purine tracts separated by one turn of the DNA helix (10 bp) were targeted by oligonucleotides containing two pyrimidine tracts (T and 'C) connected by a central T linker of size 2–9. It has been previously shown that such oligonucleotides bend DNA to a varying degree dependent upon the size of the linker (Liberles, D. A. & Dervan, P. B. (I 996) Proc. Natl. Acad. Sci., USA 93, 9510–4). The intervening 10 bp not targeted by the third strand oligonucleotide can be bound by a polyamide specifically designed for that sequence, as depicted in FIGS. 13 and 14. The binding affinity of the polyamide for its target sequence has previously been determined under similar conditions and reported to be 3.7×10$^{10}$ M$^{-1}$ for PA1 and 5.0×10$^8$ M$^{-1}$ for PA2, both much stronger than the affinity of either the unlinked 15 mers for their sites, or the linked bidentate oligonucleotides (Liberles, D. A. & Dervan, P. B. (1996) Proc. Natl. Acad. Sci., USA 93, 9510–4); Liberles, D. A. & Dervan, P. B., unpublished data; Trauger, J. W., Baird, E. E. & Dervan, P. B. (1996) Nature 382, 559–61). Given the ability of polyamides to straighten DNA, it is demonstrated herein that targeting a polyamide to the intervening duplex of bent DNA can straighten it, displacing a ligand bound several base pairs distally, as depicted in FIG. 15.

Figure 16A:
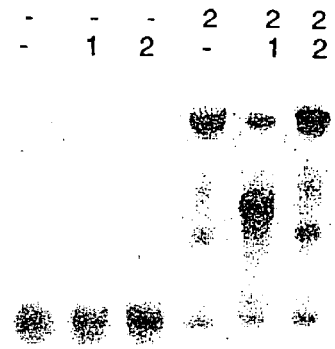
FIG. 16. Gel shift analysis of oligonucleotide 2 on a $3'^{32}P$ end-labeled restriction fragment generated with EcoRI and HindIII.
Figure 16B:

PA1 at a concentration of 100 pM can displace a DNA bending third strand oligonucleotide at a concentration of 1 $\mu$M. This effect is clearly seen in FIG. 16 for oligonucleotides with linkers of 2 and 3 T residues, bending DNA greater than 600. In these lanes, the more retarded bent structure is shifted to a less retarded structure with mobility similar to a double Y structure, where two oligonucleotides are bound by a single target DNA molecule with the polyamide presumably bound between them. For oligonucleotides with smaller bend angles, the polyamide does not displace the third strand oligonucleotide and the DNA distortion is probably not sufficient to preclude efficient polyamide binding. The specificity of this effect is seen in FIGS. 17A and 17B, where only PA1, but not PA2 can displace oligonucleotide 2 at a concentration of 100 pM, while neither can displace oligonucleotide 9.

These experiments were performed with simultaneous addition of polyamide and oligonucleotide. Next, we sought to determine if the order of addition was important given the reported half life of a bound third strand oligonucleotide on DNA at approximately 12 hours under near physiological conditions (Maher, et al. (1990) Biochemistry 29, 8820–8826). As shown in FIG. 18, simultaneous addition, preincubation with polyamide for one hour, or preincubation with third strand oligonucleotide for 1 hour made little difference in the ability of the polyamide to inhibit binding of the third strand oligonucleotide, where 1 hour is less than expected association rate for both oligonucleotide and polyamide (Maher, L. J., Dervan, P. B. & Wold, B. J. (I 990) Biochemistry 29, 8820–8826; Albert, et al. (1997), submitted). As such, polyamides may be useful in targeting prebound transcription factors in cells.

Figure 17:
FIG. 17. Gel shift analysis of oligonucleotide 2 on a $3'^{32}P$ end-labeled restriction fragment generated with EcoRI and HindIII.

It has been shown that the energy required to bend DNA with bidentate triple helical ligands is less than predicted by theoretical models of DNA as a smoothly bending wormlike chain with coulombic repulsion from phosphates placed at fixed distances (Akiyama, T. & Hogan, M. E. (1996) J. Biological Chemistry 271, 29126–29135; Liberles, D. A. & Dervan, P. B., unpublished data; Bloomfield, et al. (1974) in Physical Chemistry of Nucleic Acids (Harper and Row, New York), pp. 159–166; Fenley, et al. (1992) J Physical Chemistry 96, 3963–3969). However, the prebending of target DNA for TBP, a general transcription factor, significantly altered its binding affinity (Parvin, et al. (1995) Nature 373, 724–727). The effects of prebending on the affinity of the polyamide by measuring the Ka, against triplex mediated bending was determined. FIG. 17 shows a sample gel shift titration, where the measured Ka, for PA1 is 6.2 (±0.3)× 10$^{\wedge 10}$, whereas K, for PA2 is <1×10$^9$ M$^{-1}$. Ka, for PA1 is within experimental error of Ka measured by DNase I footprinting and shows that the energy for straightening DNA bent by a ligand with a lower binding affinity is minimal (Trauger, et al. (1996) Nature 382, 559–61). Bending effects with TBP may be much larger, given the large number of protein-DNA contacts supporting the bent structure (Kim, et al. (1993) Nature 365, 512–520; Bond, et al. (1994) Biophysical Journal 67, 825–836). Additionally, TBP-bound DNA is bent towards the major groove, not the minor groove.

To confirm that binding of the polyamide is indeed in the intervening duplex, DNase I and MPE footprinting were performed, as shown in FIG. 17. While no binding in the intervening duplex and no displacement of the third strand oligonucleotide are seen for PA2, PA1 dislodges the third strand oligonucleotide, while protecting the intervening duplex. This supports the model of displacement of the bending ligand.

The mechanism of action of polyamides is assumed to be directly through regidification of the double helix. Alternative modes of action to be considered are simple steric blockage, or disruption of the solvation shell or counterion shell. Modeling of the triple helix-mediated bend shows a linker that is displaced from the intervening duplex to accomodate the bend angle, where shorter linkers are displaced further from the duplex than longer linkers. The inability of PA1 to displace bending oligonucleotides with longer linkers and bend angles less than 600 degrees argues against this explanation. Disruption of the salvation shell in the minor groove is likely to be steric and therefore unlikely to extend into the triple helical region where no polyamide is bound. Furthermore, this minor groove effect is unlikely to effect binding of a third strand in the major groove, where simultaneous binding has previously been demonstrated (Parks, et al. (1996) Bioorganic & Medicinal Chemistry 4, 1045–50). Similarly, the high charge density of double helical and triple helical DNA results in a large counterion shell around the molecule and in a very short Debye screening length where charge effects are unlikely to extend for multiple base pairs (Bond, et al. (1994) Biophysical Journal 67, 825–836; Philpott, et al. (1995) J. Electrochem. Soc. 142, L25–L28.).

By modifying DNA structure, generalizable sequence-specific polyamides have been designed to displace a DNA bending ligand at an adjacent but nonoverlapping binding site. This ability to displace DNA bending ligands through rigidification may be useful in the design of polyamides as artificial regulators of gene expression, providing a potentially valuable tool in molecular biology and human medicine.

As disclosed herein, the present invention provides the reagents and methodologies for the preparation and use of a variety of new polyamides comprising positive patch sequences for specific recognition of DNA in the minor groove and inhibiting the function of DNA-binding proteins that bind the major groove. Also provided is a methodology for determining the mechanism of action of inhibition of DNA-binding molecules. While a preferred form of the invention has been shown in the drawings and described, since variations in the preferred form will be apparent to those skilled in the art, the invention should not be construed as limited to the specific form shown and described, but instead is as set forth in the claims.

We claim:

1. A polyamide molecule that specifically binds to base pairs in the minor groove of a DNA molecule, said polyamide molecule comprising:
   one or more amino acids comprising a moiety selected from the group consisting of N-methylpyrrole, 3-hydroxy-N-methylpyrrole, and N-methylimidazole, wherein one or more of said amino acid(s) are not α-amino acids; and
   a positive patch consisting of a rigid group adjacent to a positively charged group, said rigid group comprising a first and a second amino acid; said first amino acid being selected from the group consisting of arginine, proline, lysine, and hydroxyproline; and said second amino acid being selected from the group consisting of proline, glycine, serine, threonine, leucine, isoleucine, valine, alanine, and hydroxyproline.

2. The polyamide of claim 1 wherein said first amino acid is arginine and said second amino acid is proline.

3. The polyamide of claim 1 wherein the positively charged group comprises a synthetic or naturally occurring amino acid having a net positive charge.

4. The polyamide of claim 1 wherein said positively charged group is selected from the group consisting of a primary amino group, secondary amino group, tertiary amino group, quartenary amino group, guanidinium group, and an amidinium group.

5. The polyamide of claim 1 wherein said positively charged group is selected from the group consisting of arginine, lysine, and histidine.

6. The polyamide of claim 1 wherein said positively charged group is arginine.

7. The polyamide of claim 1 wherein the positive patch comprises the amino acid sequence Arg-Pro-Arg.

8. The polyamide of claim 1 wherein the polyamide has three or four carboxyamide binding pairs.

9. The polyamide of claim 1 wherein the polyamide comprises an (R)-2,4-diaminobutyric acid hairpin turn that facilitates specific binding to base pairs in the minor groove of a DNA molecule.

10. The polyamide of claim 9 wherein the R-2-amino group is derivatized to form an acid amide.

11. The polyamide of claim 1 having the formula:

$$X_1X_2X_3\gamma X_4X_5X_6A$$

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_6$, $X_2/X_5$, and $X_3/X_4$ represent three carboxamide binding pairs which bind DNA base pairs and are selected from the group consisting of 3-hydroxy-N-methylpyrrole/N-methylpyrrole (Hp/Py), N-methylpyrrole/3-hydroxy-N-methylpyrrole (Py/Hp), N-methylpyrrole/N-methylimidazole (Py/Im), N-methylimidazole/N-methylimidazole (Im/Py), and N-methylpyrrole/N-methylpyrrole (Py/Py) to correspond to the DNA base pair in the minor groove to be bound; and A represents said positive patch consisting of a rigid group adjacent to a positively charged group.

12. The polyamide of claim 11 wherein the positive patch comprises the amino acid sequence Arg-Pro-Arg.

13. The polyamide of claim 1 having the formula:

$$X_1X_2X_3X_4\gamma X_5X_6X_7X_8A$$

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_8$, $X_2/X_7$, $X_3/X_6$, and $X_4/X_5$ represent four carboxamide binding pairs which bind DNA base pairs and are selected from the group consisting of Hp/Py, Py/Hp, Py/Im, Im/Py, and Py/Py to correspond to the DNA base pair in the minor groove to be bound; and A represents said positive patch consisting of a rigid group adjacent to a positively charged group.

14. The A polyamide of claim 13 wherein the positive patch comprises the amino acid sequence Arg-Pro-Arg.

15. The polyamide of claim 1 having the formula:

$$X_1X_2X_3X_4X_5\gamma X_6X_7X_8X_9X_{10}A$$

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_{10}$, $X_2/X_9$, $X_3/X_8$, $X_4/X_7$, and $X_5/X_6$ represent five carboxamide binding pairs which bind DNA base pairs and are selected from the group consisting of Hp/Py, Py/Hp, Py/Im, Im/Py, and Py/Py to correspond to the DNA base pair in the minor groove to be bound; and A represents said positive patch consisting of a rigid group adjacent to a positively charged group.

16. The polyamide of claim 15 wherein the positive patch comprises the amino acid sequence Arg-Pro-Arg.

17. The polyamide of claim 1 having the formula:

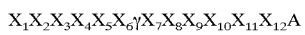

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_{12}$, $X_2/X_{11}$, $X_3/X_{10}$, $X_4/X_9$, $X_5/X_8$, and $X_6/X_7$ represent six carboxamide binding pairs which bind DNA base pairs and are selected from the group consisting of Hp/Py, Py/Hp, Py/Im, Im/Py, and Py/Py to correspond to the DNA base pair in the minor groove to be bound; and A represents said positive patch consisting of a rigid group adjacent to a positively charged group.

18. The polyamide of claim 17 wherein the positive patch comprises the amino acid sequence Arg-Pro-Arg.

19. A tandem-linked polyamide having the formula:

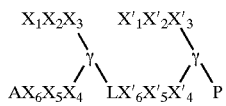

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_6$, $X_2/X_5$, $X_3/X_4$, $X'_1/X'_6$, $X'_2/X'_5$, and $X'_3/X'_4$ represent carboxamide binding pairs which bind DNA base pairs and are selected from the group consisting of Hp/Py, Py/Hp, Py/Im, Im/Py, and Py/Py to correspond to the DNA base pair in the minor groove to be bound;

L represents an amino acid linking group selected from the group consisting of β-alanine and 5-aminovaleric acid (δ);

P represents a polyamide selected from the group consisting of $X_1X_2X_3\gamma X_4X_5X_6$, $X_1X_2X_3X_4\gamma X_5X_6X_7X_8$, $X_1X_2X_3X_4X_5\gamma X_6X_7X_8X_9X_{10}$, and $X_1X_2X_3X_4X_5X_6\gamma X_7X_8X_9X_{10}X_{11}X_{12}$, where $X_1$–$X_{12}$ are independently selected from the group consisting of β-alanine, pyrrole, hydroxypyrrole and imidazole; and A represents a positive patch consisting of a rigid group adjacent to a positively charged group.

20. A tandem-linked polyamide having the formula:

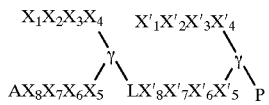

wherein γ is —NH—CH$_2$—CH$_2$—CH$_2$—CONH— hairpin linkage derived from γ aminobutyric acid or a chiral hairpin linkage derived from 2,4-diaminobutyric acid;

$X_1/X_8$, $X_2/X_7$, $X_3/X_6$, $X_4/X_5$, $X'_1/X'_8$, $X'_2/X'_7$, $X'_3/X'_6$, and $X'_4/X'_5$, represent carboxamide binding pairs which bind DNA base pairs and are selected from the group consisting of Hp/Py, Py/Hp, Py/Im, Im/Py, and Py/Py to correspond to the DNA base pair in the minor groove to be bound;

L represents an amino acid linking group selected from the group consisting of β-alanine and 5-aminovaleric acid (δ);

P represents a polyamide selected from the group consisting of $X_1X_2X_3\gamma X_4X_5X_6$, $X_1X_2X_3X_4\gamma X_5X_6X_7X_8$, $X_1X_2X_3X_4X_5\gamma X_6X_7X_8X_9X_{10}$, and $X_1X_2X_3X_4X_5X_6\gamma X_7X_8X_9X_{10}X_{11}X_{12}$, where $X_1$–$X_{12}$ are independently selected from the group consisting of β-alanine, pyrrole, hydroxypyrrole and imidazole; and A represents a positive patch consisting of a rigid group adjacent to a positively charged group.

21. A tandem-linked polyamide having the formula:

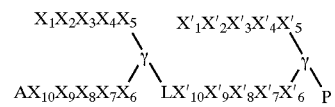

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_{10}$, $X_2/X_9$, $X_3/X_8$, $X_4/X_7$, $X_5/X_6$, $X'_1/X'_{10}$, $X'_2/X'_9$, $X'_3/X'_8$, $X'_4/X'_7$, and $X'_5/X'_6$ represent carboxamide binding pairs which bind DNA base pairs and are selected from the group consisting of $H_p/P_y$, $P_y/H_p$, $P_y/I_m$, $I_m/P_y$, and $P_y/P_y$ to correspond to the DNA base pair in the minor groove to be bound;

L represents an amino acid linking group selected from the group consisting of β-alanine and 5-aminovaleric acid (δ);

P represents a polyamide selected from the group consisting of $X_1X_2X_3\gamma X_4X_5X_6$, $X_1X_2X_3X_4\gamma X_5X_6X_7X_8$, $X_1X_2X_3X_4X_5\gamma X_6X_7X_8X_9X_{10}$, and $X_1X_2X_3X_4X_5X_6\gamma X_7X_8X_9X_{10}X_{11}X_{12}$, where $X_1$–$X_{12}$ are independently selected from the group consisting of β-alanine, pyrrole, hydroxypyrrole and imidazole; and A represents a positive patch consisting of a rigid group adjacent to a positively charged group.

22. A tandem-linked polyamide having the formula:

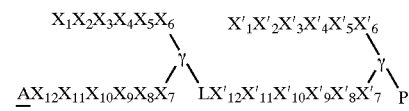

wherein γ is —NH—CH$_2$—CH$_2$—CH$_2$—CONH— hairpin linkage derived from γ-aminobutyric acid or a chiral hairpin linkage derived from 2,4-diaminobutyric acid;

$X_1/X_{12}$, $X_2/X_{11}$, $X_3/X_{10}$, $X_4/X_9$, $X_5/X_8$, $X_6/X_7$, $X'_1/X'_{12}$, $X'_2/X'_{11}$, $X'_3/X'_{10}$, $X'_4/X'_9$, $X'_5/X'_8$, and $X'_6/X'_7$ represent carboxamide binding pairs which bind DNA base pairs and are selected from the group consisting of Hp/Py, Py/Hp, Py/Im, Im/Py, and Py/Py to correspond to the DNA base pair in the minor groove to be bound;

L represents an amino acid linking group selected from the group consisting of β-alanine and 5-aminovaleric acid (δ);

P represents a polyamide selected from the group consisting of $X_1X_2X_3\gamma X_4X_5X_6$, $X_1X_2X_3X_4\gamma X_5X_6X_7X_8$, $X_1X_2X_3X_4X_5\gamma X_6X_7X_8X_9X_{10}$, and $X_1X_2X_3X_4X_5X_6\gamma X_7X_8X_9X_{10}X_{11}X_{12}$, where $X_1$–$X_{12}$ are independently selected from the group consisting of β-alanine, pyrrole, hydroxypyrrole and imidazole; and A represents a positive patch consisting of a rigid group adjacent to a positively charged group.

23. The polyamide of claim 1 selected the group consisting of:

ImPyPyPy-γ-PyPyPyPy-β-RPR;

ImImPyPy-γ-ImPyPyPy-β-RPR;

ImPyPyPy-γ-PyPyPyPy-β-RPRRRR;

ImImPyPy-γ-ImPyPyPy-β-RPRRRR;

ImPyPyPy-γ-PyPyPyPy-β-R;

ImPyPyPy-γ-PyPyPyPy-β-RP;

ImPyPyPy-γ-PyPyPyPy-β-RGR;

ImPyPyPy-γ-PyPyPyPy-β-R$^D$PR;

ImPyPyPy-γ-PyPyPyPy-β-APR;

ImPyPyPy-γ-PyPyPyPy-β-KPR;

ImPyPyPy-γ-PyPyPyPy-β-RPK;

ImPyPyPy-γ-PyPyPyPy-β-C7-RPR; and the pharmaceutically acceptable salts thereof.

24. A method of inhibiting gene expression comprising contacting a regulatory sequence of a gene with the polyamide of claim 1.

25. A method of inhibiting gene expression comprising contacting a DNA molecule with the polyamide of claim 1 whereby the DNA molecule is conformationally constrained.

* * * * *

UNITED STATES PATENT AND TRADEMARK OFFICE
CERTIFICATE OF CORRECTION

PATENT NO.   : 6,958,240 B1
DATED        : October 25, 2005
INVENTOR(S)  : Eldon E. Baird and Peter B. Dervan It is certified that error appears in the above-identified patent and that said Letters Patent is hereby corrected as shown below:

Column 34,
Lines 29-30, replace "$H_p/P_y$, $P_y/H_p$, $P_y/I_m$, $I_m/P_y$, and $P_y/P_y$" with
-- Hp/Py, Py/Hp, Py/Im, Im/Py, and Py/Py --.

Signed and Sealed this

Twenty-first Day of March, 2006

JON W. DUDAS
*Director of the United States Patent and Trademark Office*

SEQUENCE LISTING

```
<160> NUMBER OF SEQ ID NOS: 20

<210> SEQ ID NO 1
<211> LENGTH: 15
<212> TYPE: DNA
<213> ORGANISM: Homo sapiens
<220> FEATURE:
<223> OTHER INFORMATION: Polyamide Motif

<400> SEQUENCE: 1
tgcctgacta atagt                                                         15

<210> SEQ ID NO 2
<211> LENGTH: 15
<212> TYPE: DNA
<213> ORGANISM: Homo sapiens
<220> FEATURE:
<223> OTHER INFORMATION: Polyamide Motif

<400> SEQUENCE: 2
actattagtc aggca                                                         15

<210> SEQ ID NO 3
<211> LENGTH: 17
<212> TYPE: DNA
<213> ORGANISM: Homo sapiens
<220> FEATURE:
<223> OTHER INFORMATION: Polyamide Motif

<400> SEQUENCE: 3
gctgactaat tgttatc                                                       17

<210> SEQ ID NO 4
<211> LENGTH: 17
<212> TYPE: DNA
<213> ORGANISM: Homo sapiens
<220> FEATURE:
<223> OTHER INFORMATION: Polyamide Motif

<400> SEQUENCE: 4
gataacaatt agtcagc                                                       17

<210> SEQ ID NO 5
<211> LENGTH: 45
<212> TYPE: DNA
<213> ORGANISM: Artificial Sequence
<220> FEATURE:
<223> OTHER INFORMATION: Synthesized DNA Fragment

<400> SEQUENCE: 5
ccggatccat ggttgctgac taattgttat cctctagagt cgacc                        45

<210> SEQ ID NO 6
```

```
<211> LENGTH: 45
<212> TYPE: DNA
<213> ORGANISM: Artificial Sequence
<220> FEATURE:
<223> OTHER INFORMATION: Synthesized DNA Fragment

<400> SEQUENCE: 6
ccagctgaga tctcctctgg ttaatcagtc gttggtacct aggcc         45

<210> SEQ ID NO 7
<211> LENGTH: 6
<212> TYPE: PRT
<213> ORGANISM: Homo sapiens
<220> FEATURE:
<223> OTHER INFORMATION: Polyamide Motif

<400> SEQUENCE: 7

Arg Pro Arg Arg Arg Arg
 1               5

<210> SEQ ID NO 8
<211> LENGTH: 20
<212> TYPE: DNA
<213> ORGANISM: Homo sapiens
<220> FEATURE:
<223> OTHER INFORMATION: Polyamide Motif

<400> SEQUENCE: 8
ttgctgacta attgttatcc                                     20

<210> SEQ ID NO 9
<211> LENGTH: 20
<212> TYPE: DNA
<213> ORGANISM: Homo sapiens
<220> FEATURE:
<223> OTHER INFORMATION: GCN4 binding molecule

<400> SEQUENCE: 9
ggataacaat tagtcagcaa                                     20

<210> SEQ ID NO 10
<211> LENGTH: 20
<212> TYPE: DNA
<213> ORGANISM: Homo sapiens
<220> FEATURE:
<223> OTHER INFORMATION: Polyamide Motif

<400> SEQUENCE: 10
ttgctgacta attggtctcc                                     20

<210> SEQ ID NO 11
<211> LENGTH: 20
<212> TYPE: DNA
<213> ORGANISM: Homo sapiens
<220> FEATURE:
<223> OTHER INFORMATION: GCN4 binding molecule

<400> SEQUENCE: 11
ggagaccaat tagtcagcaa                                     20

<210> SEQ ID NO 12
<211> LENGTH: 13
<212> TYPE: DNA
<213> ORGANISM: Homo sapiens
<220> FEATURE:
<223> OTHER INFORMATION: Polyamide Motif
```

```
<400> SEQUENCE: 12
aatcatggtc ata                                                          13

<210> SEQ ID NO 13
<211> LENGTH: 13
<212> TYPE: DNA
<213> ORGANISM: Homo sapiens
<220> FEATURE:
<223> OTHER INFORMATION: GCN4 binding molecule

<400> SEQUENCE: 13
tatgaccatg att                                                          13

<210> SEQ ID NO 14
<211> LENGTH: 13
<212> TYPE: DNA
<213> ORGANISM: Homo sapiens
<220> FEATURE:
<223> OTHER INFORMATION: Polyamide Motif

<400> SEQUENCE: 14
ctcattggac agc                                                          13

<210> SEQ ID NO 15
<211> LENGTH: 13
<212> TYPE: DNA
<213> ORGANISM: Homo sapiens
<220> FEATURE:
<223> OTHER INFORMATION: GCN4 binding molecule

<400> SEQUENCE: 15
gctgtccaat gag                                                          13

<210> SEQ ID NO 16
<211> LENGTH: 13
<212> TYPE: DNA
<213> ORGANISM: Homo sapiens
<220> FEATURE:
<223> OTHER INFORMATION: Polyamide Motif

<400> SEQUENCE: 16
ctcattgtac agc                                                          13

<210> SEQ ID NO 17
<211> LENGTH: 13
<212> TYPE: DNA
<213> ORGANISM: Homo sapiens
<220> FEATURE:
<223> OTHER INFORMATION: GCN4 binding molecule

<400> SEQUENCE: 17
gctgtacaat gag                                                          13

<210> SEQ ID NO 18
<211> LENGTH: 31
<212> TYPE: DNA
<213> ORGANISM: Homo sapiens
<220> FEATURE:
<223> OTHER INFORMATION: Polyamide Motif

<400> SEQUENCE: 18
tctctcctcc tctctttcct ctctctctcc t                                      31

<210> SEQ ID NO 19
<211> LENGTH: 40
```

```
-continued
<212> TYPE: DNA
<213> ORGANISM: Homo sapiens
<220> FEATURE:
<223> OTHER INFORMATION: GCN4 binding molecule

<400> SEQUENCE: 19
aggagagaga gaggatatca tgaacagaga ggaggagaga                              40

<210> SEQ ID NO 20
<211> LENGTH: 40
<212> TYPE: DNA
<213> ORGANISM: Homo sapiens
<220> FEATURE:
<223> OTHER INFORMATION: Polyamide Motif

<400> SEQUENCE: 20
tctctcctcc tctctgttca tgatatcctc tctctctcct                              40
```